US011596798B2

(12) United States Patent
Thacker et al.

(10) Patent No.: US 11,596,798 B2
(45) Date of Patent: Mar. 7, 2023

(54) TREATMENT OF CONGESTIVE HEART FAILURE WITH ELECTRICAL STIMULATION, AND ASSOCIATED SYSTEMS AND METHODS

(71) Applicant: Nevro Corp., Redwood City, CA (US)

(72) Inventors: James R. Thacker, Homer, AK (US); Kerry Bradley, Glendale, CA (US)

(73) Assignee: Nevro Corp, Redwood City, CA (US)

( * ) Notice: Subject to any disclaimer, the term of this patent is extended or adjusted under 35 U.S.C. 154(b) by 343 days.

(21) Appl. No.: 17/030,349

(22) Filed: Sep. 23, 2020

(65) Prior Publication Data

US 2021/0060338 A1 Mar. 4, 2021

Related U.S. Application Data

(62) Division of application No. 15/414,561, filed on Jan. 24, 2017, now abandoned.

(60) Provisional application No. 62/286,892, filed on Jan. 25, 2016.

(51) Int. Cl.
*A61N 1/362* (2006.01)
*A61N 1/36* (2006.01)
*A61N 1/05* (2006.01)

(52) U.S. Cl.
CPC ........ *A61N 1/3627* (2013.01); *A61N 1/36114* (2013.01); *A61N 1/36139* (2013.01); *A61N 1/36171* (2013.01); *A61N 1/056* (2013.01)

(58) Field of Classification Search
None
See application file for complete search history.

(56) References Cited

U.S. PATENT DOCUMENTS

| 1,597,061 | A | 8/1926 | Cultra |
| 3,195,540 | A | 7/1965 | Waller |
| 3,724,467 | A | 4/1973 | Avery et al. |

(Continued)

FOREIGN PATENT DOCUMENTS

| CN | 101175530 | 5/2008 |
| DE | 10318071 A1 | 11/2004 |

(Continued)

OTHER PUBLICATIONS

Cadish, "Stimulation Latency and Comparison of Cycling Regimens in Women Using Sacral Neuromodulation," Feb. 1, 2016, 4 pages.

(Continued)

*Primary Examiner* — Mark W. Bockelman
(74) *Attorney, Agent, or Firm* — Perkins Coie LLP

(57) ABSTRACT

Systems and methods for treating congestive heart failure with high frequency stimulation are disclosed. A representative method for treating a patient includes applying an electrical signal having a frequency of from about 1 kHz to about 100 kHz to the patient via a treatment system that includes a signal delivery element in electrical communication with the patient's vagus nerve at a portion of the vagus nerve located at or proximate to the anterior interventricular junction of the patient's heart. The method can further include automatically detecting at least one physiological parameter of the patient, automatically determining at least one of an ejection fraction of the patient's heart and a correlate of the ejection fraction based on the detected parameter, and automatically adjusting the applied signal based on the determined ejection fraction.

22 Claims, 6 Drawing Sheets

(56) References Cited

U.S. PATENT DOCUMENTS

| | | |
|---|---|---|
| 3,727,616 A | 4/1973 | Lenzkes |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |
| 4,379,462 A | 4/1983 | Borkan et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,612,934 A | 9/1986 | Borkan et al. |
| 4,649,935 A | 3/1987 | Charmillot et al. |
| 4,735,204 A | 4/1988 | Sussman et al. |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill |
| 5,335,657 A | 8/1994 | Terry, Jr. et al. |
| 5,354,320 A | 10/1994 | Schaldach et al. |
| 5,514,175 A | 5/1996 | Kim et al. |
| 5,540,734 A | 7/1996 | Zabara |
| 5,562,717 A | 10/1996 | Tippey |
| 5,643,330 A | 7/1997 | Holsheimer et al. |
| 5,716,377 A | 2/1998 | Rise et al. |
| 5,755,758 A | 5/1998 | Wolozko |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,938,690 A | 8/1999 | Law |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,049,701 A | 4/2000 | Sparksman |
| 6,161,044 A | 12/2000 | Silverstone |
| 6,161,048 A | 12/2000 | Sluijter et al. |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,473,644 B1 | 10/2002 | Terry, Jr. et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,587,724 B2 | 7/2003 | Mann |
| 6,609,030 B1 | 8/2003 | Rezai et al. |
| 6,622,048 B1 | 9/2003 | Mann et al. |
| 6,659,968 B1 | 12/2003 | McClure |
| 6,662,051 B1 | 12/2003 | Eraker et al. |
| 6,714,822 B2 | 3/2004 | King et al. |
| 6,721,603 B2 | 4/2004 | Zabara et al. |
| 6,795,737 B2 | 9/2004 | Gielen et al. |
| 6,856,315 B2 | 2/2005 | Eberlein |
| 6,871,090 B1 | 3/2005 | He et al. |
| 6,871,099 B1 | 3/2005 | Whitehurst et al. |
| 6,885,888 B2 | 4/2005 | Rezai |
| 6,907,293 B2 | 6/2005 | Grill et al. |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,162,304 B1 | 1/2007 | Bradley |
| 7,167,750 B2 | 1/2007 | Knudson et al. |
| 7,174,215 B2 | 2/2007 | Bradley |
| 7,177,702 B2 | 2/2007 | Wallace et al. |
| 7,180,760 B1 | 2/2007 | Varrichio et al. |
| 7,206,640 B1 | 4/2007 | Overstreet |
| 7,212,865 B2 | 5/2007 | Cory |
| 7,225,035 B2 | 5/2007 | Brabec et al. |
| 7,236,822 B2 | 6/2007 | Dobak, III |
| 7,236,830 B2 | 6/2007 | Gliner |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,463,927 B1 | 12/2008 | Chaouat |
| 7,483,747 B2 | 1/2009 | Gliner et al. |
| 7,493,172 B2 | 2/2009 | Whitehurst et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,715,915 B1 | 5/2010 | Rye et al. |
| 7,734,340 B2 | 6/2010 | De Ridder |
| 7,734,355 B2 | 6/2010 | Cohen et al. |
| 7,742,810 B2 | 6/2010 | Moffitt et al. |
| 7,761,170 B2 | 7/2010 | Kaplan et al. |
| 7,778,704 B2 | 8/2010 | Rezai |
| 7,792,591 B2 | 9/2010 | Rooney et al. |
| 7,801,604 B2 | 9/2010 | Brockway et al. |
| 7,813,803 B2 | 10/2010 | Heruth et al. |
| 7,826,901 B2 | 11/2010 | Lee et al. |
| 7,853,322 B2 | 12/2010 | Bourget et al. |
| 7,860,570 B2 | 12/2010 | Whitehurst et al. |
| 7,865,243 B1 | 1/2011 | Whitehurst et al. |
| 7,877,136 B1 | 1/2011 | Moffitt et al. |
| 7,877,146 B2 | 1/2011 | Rezai |
| 7,881,805 B2 | 2/2011 | Bradley |
| 7,890,176 B2 | 2/2011 | Jaax et al. |
| 7,890,182 B2 | 2/2011 | Parramon et al. |
| 7,914,452 B2 | 3/2011 | Hartley et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |

(56) References Cited

U.S. PATENT DOCUMENTS

| | | |
|---|---|---|
| 8,082,039 B2 | 12/2011 | Kim et al. |
| 8,150,531 B2 | 4/2012 | Skelton |
| 8,170,658 B2 | 5/2012 | Dacey et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,224,459 B1 | 7/2012 | Pianca et al. |
| 8,255,048 B2 | 8/2012 | Dal Molin et al. |
| 8,280,515 B2 | 10/2012 | Greenspan et al. |
| 8,301,241 B2 | 10/2012 | Ternes et al. |
| 8,340,775 B1 | 12/2012 | Cullen et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 2,622,601 A1 | 3/2013 | Alataris et al. |
| 8,396,559 B2 | 3/2013 | Alataris et al. |
| 8,412,338 B2 | 4/2013 | Faltys |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,483,830 B2 | 7/2013 | Tweden |
| 8,569,935 B1 | 10/2013 | Kosierkiewicz |
| 8,577,458 B1 | 11/2013 | Libbus et al. |
| 8,612,018 B2 | 12/2013 | Gillbe |
| 8,649,874 B2 | 2/2014 | Alataris et al. |
| 8,666,506 B2 | 3/2014 | King |
| 8,688,212 B2 | 4/2014 | Libbus et al. |
| 8,691,877 B2 | 4/2014 | Yun et al. |
| 8,712,533 B2 | 4/2014 | Alataris |
| 8,751,009 B2 | 6/2014 | Wacnik |
| 8,768,469 B2 | 7/2014 | Tweden et al. |
| 8,768,472 B2 | 7/2014 | Fang |
| 8,805,512 B1 | 8/2014 | Greiner et al. |
| 8,825,164 B2 | 9/2014 | Tweden et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 8,918,191 B2 | 12/2014 | Libbus et al. |
| 8,923,964 B2 | 12/2014 | Libbus et al. |
| 8,923,990 B2 | 12/2014 | Libbus et al. |
| 8,965,521 B2 | 2/2015 | Birkholz et al. |
| 8,996,125 B2 | 3/2015 | Greiner et al. |
| 9,002,457 B2 | 4/2015 | Hamann et al. |
| 9,002,459 B2 | 4/2015 | Lee et al. |
| 9,026,214 B2 | 5/2015 | Ternes et al. |
| 9,026,215 B2 | 5/2015 | Rossing |
| 9,026,226 B2 | 5/2015 | Gerber et al. |
| 9,067,076 B2 | 6/2015 | Nolan et al. |
| 9,101,770 B2 | 8/2015 | Arcot-Krishnamurthy et al. |
| 9,126,044 B2 | 9/2015 | Kramer et al. |
| 9,132,272 B2 | 9/2015 | Alves et al. |
| 9,180,298 B2 | 11/2015 | Alataris et al. |
| 9,205,258 B2 | 12/2015 | Simon et al. |
| 9,211,410 B2 | 12/2015 | Levine et al. |
| 9,295,840 B1 | 3/2016 | Thacker |
| 9,308,370 B2 | 4/2016 | Lima et al. |
| 9,327,121 B2 | 5/2016 | Bertram |
| 9,327,127 B2 | 5/2016 | Alataris et al. |
| 9,370,659 B2 | 6/2016 | Franke et al. |
| 9,381,356 B2 | 7/2016 | Parker |
| 9,403,007 B2 | 8/2016 | Moekelke et al. |
| 9,421,355 B2 | 8/2016 | Colborn |
| 9,440,074 B2 | 9/2016 | Ternes et al. |
| 9,480,846 B2 | 11/2016 | Strother |
| 9,533,153 B2 | 1/2017 | Libbus et al. |
| 9,561,366 B2 | 2/2017 | Wei et al. |
| 9,561,370 B2 | 2/2017 | Rezai |
| 9,572,983 B2 | 2/2017 | Levine et al. |
| 9,694,183 B2 | 7/2017 | Grandhe |
| 9,724,509 B2 | 8/2017 | Su et al. |
| 9,724,511 B2 | 8/2017 | Wei et al. |
| 9,833,614 B1 | 12/2017 | Gliner |
| 9,895,532 B2 | 2/2018 | Kaula et al. |
| 9,895,539 B1 | 2/2018 | Heit et al. |
| 9,913,980 B2 | 3/2018 | Ostroff et al. |
| 9,950,173 B2 | 4/2018 | Doan |
| 9,968,732 B2 | 5/2018 | Drew et al. |
| 10,188,856 B1 | 1/2019 | Libbus et al. |
| 10,207,110 B1 | 2/2019 | Gelfand |
| 10,220,205 B2 | 3/2019 | Bhadra et al. |
| 10,328,264 B2 | 6/2019 | Hamann et al. |
| 10,485,975 B2 | 11/2019 | Greiner et al. |
| 10,493,275 B2 | 12/2019 | Alataris |
| 10,561,845 B2 | 2/2020 | Giftakis et al. |
| 10,632,300 B2 | 4/2020 | Wagenbach et al. |
| 10,675,468 B2 | 6/2020 | Torgerson |
| 10,898,714 B2 | 1/2021 | Libbus et al. |
| 11,045,649 B2 | 6/2021 | Wei et al. |
| 2002/0055779 A1 | 5/2002 | Andrews |
| 2002/0087201 A1 | 7/2002 | Firlik et al. |
| 2002/0128700 A1 | 9/2002 | Cross |
| 2003/0100931 A1 | 5/2003 | Mullett |
| 2003/0120323 A1 | 6/2003 | Meadows et al. |
| 2003/0135248 A1 | 7/2003 | Stypulkowski |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0122477 A1 | 6/2004 | Whitehorse |
| 2004/0158298 A1 | 8/2004 | Gliner |
| 2004/0162590 A1 | 8/2004 | Whitehurst et al. |
| 2004/0167584 A1 | 8/2004 | Carroll et al. |
| 2004/0186532 A1 | 9/2004 | Tadlock |
| 2004/0193228 A1 | 9/2004 | Gerber |
| 2004/0210270 A1 | 10/2004 | Erickson |
| 2004/0210271 A1 | 10/2004 | Campen et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143783 A1 | 6/2005 | Boveja |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0222641 A1 | 10/2005 | Pless |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0074456 A1 | 4/2006 | Pyles et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167525 A1 | 7/2006 | King |
| 2006/0168805 A1 | 8/2006 | Hegland et al. |
| 2006/0190044 A1 | 8/2006 | Libbus et al. |

(56) References Cited

U.S. PATENT DOCUMENTS

| | | |
|---|---|---|
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2006/0271108 A1 | 11/2006 | Libbus et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0100388 A1 | 5/2007 | Gerber |
| 2007/0106337 A1 | 5/2007 | Errico et al. |
| 2007/0106342 A1 | 5/2007 | Schumann |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0156201 A1 | 7/2007 | Rossing |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0191902 A1 | 8/2007 | Errico |
| 2007/0203537 A1 | 8/2007 | Goetz et al. |
| 2007/0213789 A1 | 9/2007 | Nolan et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265681 A1 | 11/2007 | Gerber et al. |
| 2007/0293893 A1 | 12/2007 | Stolen et al. |
| 2007/0299482 A1 | 12/2007 | Littlewood et al. |
| 2008/0033511 A1 | 2/2008 | Dobak |
| 2008/0065158 A1 | 3/2008 | Ben-Ezra |
| 2008/0086036 A1 | 4/2008 | Hartley |
| 2008/0097539 A1 | 4/2008 | Belalcazar |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2008/0300449 A1 | 12/2008 | Gerber |
| 2008/0319511 A1 | 12/2008 | Pless |
| 2009/0018617 A1 | 1/2009 | Skelton et al. |
| 2009/0024187 A1 | 1/2009 | Erickson et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0083070 A1 | 3/2009 | Giftakis |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0191307 A1 | 7/2010 | Fang et al. |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0010680 A1 | 1/2012 | Wei |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0150252 A1 | 6/2012 | Feldman et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0079841 A1 | 3/2013 | Su |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0238047 A1 | 9/2013 | Libbus et al. |
| 2013/0261695 A1 | 10/2013 | Thacker et al. |
| 2013/0261696 A1 | 10/2013 | Alataris et al. |
| 2013/0261697 A1 | 10/2013 | Alataris et al. |
| 2013/0289659 A1 | 10/2013 | Nelson |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0296936 A1 | 10/2014 | Alataris et al. |
| 2014/0316484 A1 | 10/2014 | Edgerton |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039040 A1 | 2/2015 | Cowan et al. |
| 2015/0039049 A1 | 2/2015 | Alataris et al. |

(56) References Cited

U.S. PATENT DOCUMENTS

| | | |
|---|---|---|
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0051665 A1 | 2/2015 | Hershey et al. |
| 2015/0073510 A1 | 3/2015 | Perryman |
| 2015/0217116 A1 | 8/2015 | Parramon et al. |
| 2015/0343220 A1 | 12/2015 | Alataris et al. |
| 2016/0114165 A1 | 4/2016 | Levine et al. |
| 2016/0121119 A1 | 5/2016 | Alataris et al. |
| 2016/0256689 A1 | 9/2016 | Vallejo et al. |
| 2016/0263376 A1 | 9/2016 | Yoo et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0339239 A1 | 11/2016 | Yoo et al. |
| 2017/0050021 A1 | 2/2017 | Cosman, Sr. |
| 2017/0087369 A1 | 3/2017 | Bokil |
| 2017/0095669 A1 | 4/2017 | Libbus et al. |
| 2017/0165485 A1 | 6/2017 | Sullivan et al. |
| 2017/0209699 A1 | 7/2017 | Thacker |
| 2017/0216602 A1 | 8/2017 | Waataja et al. |
| 2017/0239470 A1 | 8/2017 | Wei et al. |
| 2017/0274209 A1 | 9/2017 | Edgerton |
| 2017/0348526 A1 | 12/2017 | Southwell |
| 2018/0110561 A1 | 4/2018 | Levin |
| 2018/0256906 A1 | 9/2018 | Pivonka |
| 2018/0272132 A1 | 9/2018 | Subbaroyan |
| 2019/0290900 A1 | 9/2019 | Esteller |
| 2019/0321641 A1 | 10/2019 | Baldoni |
| 2020/0139138 A1 | 5/2020 | Sit |

FOREIGN PATENT DOCUMENTS

| | | |
|---|---|---|
| EP | 1181947 A2 | 2/2002 |
| EP | 2243511 A2 | 10/2010 |
| EP | 2448633 A1 | 5/2012 |
| EP | 2630984 A1 | 8/2013 |
| GB | 2449546 A | 11/2008 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-20090129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2016154091 A1 | 9/2016 |
| WO | WO-2017044904 | 3/2017 |
| WO | WO-2017146658 | 8/2017 |

OTHER PUBLICATIONS

Siegel et al., "Prospective Randomized Feasibility Study Assessing the Effect of Cyclic Sacral Neuromodulation on Urinary Urge Incontinence in Women," Female Pelvic Med Reconstr Surg. 2018, 5 pages.

European Extended Search Report for European Patent Application No. 17744784.4, Applicant: Nevro Corporation, dated Oct. 8, 2019, 9 pages.

International Search Report and Written Opinion for International Patent Application No. PCT/2017/014784, dated May 1, 2017, 13 pages.

U.S. Appl. No. 14/534,769, filed Nov. 6, 2014, Park.

U.S. Appl. No. 15/606,869, filed May 26, 2017, Lee.

Abejon et al., "Is Impedance a Parameter to be Taken into Account in Spinal Cord Stimulation?" Pain Physician, 2007, 8 pages.

Agnew et al., "Considerations for safety with chronically implanted nerve electrodes," Epilepsia, 31.s2, 1990, 6 pages.

Al-Kaisy et al., "10 kHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.

Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, 2018, 9 pages.

Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural, Interface, 2015, 6 pages.

Al-Kaisy et al., Poster: "High-Frequency Spinal Cord Stimulation at 10 kHz for the Treatment of Chronic Back Pain Patients without Prior Back Surgery," 1 page.

Alo et al., "Factors Affecting Impedance of Percutaneous Leads in Spinal Cord Stimulation," International Neuromodulation Society, vol. 9, No. 2, 2006, 8 pages.

Alo et al., "New Trends in Neuromodulation for the Management of Neuropathic Pain," Neurosurgery, vol. 50, No. 4, Apr. 2002, 15 pages.

Bara et al., Poster re: High Frequency Spinal Cord Stimulation for Dominant Back Pain—1 year follow up, 2013, 1 page.

Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.

BionicNAVIGATOR Software Guide, Part MP9055261-001, 2004, 58 pages.

Bronstein et al., "The Rationale Driving the Evolution of Deep Brain Stimulation of Constant-Current Devices," International Neuromodulation Society 2014, 5 pages.

Broseta et al., "High-Frequency cervical spinal cord stimulation in spasticity and motor disorders," Advances in Stereotactic and Functional Neurosurgery 7. Springer Verlag 1987, 6 pages.

Cahana et al., "Acute Differential Modulation of Synaptic Transmission and Cell Survival During Exposure to Pulsed and Continuous Radiofrequency Energy," Journal of Pain, vol. 4, No. 4, May 2003, 6 pages.

Cameron et al., "Effects of posture on stimulation parameters in spinal cord stimulation," Neuromodulation: Technology at the Neural Interface 1.4, 1998, 8 pages.

Camilleri et al., "Intra-abdominal vagal blocking (VBLOC therapy): clinical results with a new implantable medical device," Surgery 143.6, 2008, 9 pages.

(56) References Cited

OTHER PUBLICATIONS

Crapanzano et al., "High Frequency Spinal Cord Stimulation for Complex Regional Pain Syndrome: A Case Report," Pain Physician, 2017, 6 pages.
Cuellar et al., "Effect of High Frequency Alternating Current on Spinal Afferent Nociceptive Transmission," Neuromodulation: Technology at the Neural Interface, 2012, 10 pages.
De Carolis et al., Poster: "Efficacy of Spinal Cord Stimulation (SCS) in the Treatment of Failed Back Surgery Syndrome (FBSS): a comparative study," 2013, 1 page.
De Ridder et al., U.S. Appl. No. 60/895,061, Applicant: Dirk De Ridder, filed Mar. 15, 2007, 47 pages.
Declaration of Dr. Jonathan Miller on behalf of European Patent No. 2853285, 26 pages, May 16, 2017.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Geddes, "A Short History of the electrical stimulation of excitable tissue—Including Electrotherapeutic Applications," The Physiologist, vol. 27, No. 1, Feb. 1984, 51 pages.
Gulve et al., Poster: "10kHz High Frequency Spinal Cord Stimulation: Middlesbrough Experience," 2013, 1 page.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
House et al., "Safety and Efficacy of the House/3M Cochlear Implant in Profoundly Deaf Adults," Otolaryngologic Clinics of North America, vol. 19, No. 2, May 1986, 12 pages.
International Neuromodulation Society 10th World Congress, Neuromodulation: Technology that Improves Patient Care, London, England, May 21-26, 2011, 385 pages.
Jacques et al., "Development of a New Implantable Bio-Telestimulator," Surg. Neurol., vol. 13, May 1980, 2 pages.
Jezernik et al., "Electrical Stimulation for the Treatment of Bladder Dysfunction: Current Status and Future Possibilities," Neurological Research, vol. 24, Jul. 2002, 18 pages.
Kapural et al., "Comparison of 10-kHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Lambru et al., "Safety and Efficacy of Cervical 10 kHz Spinal Cord Stimulation in Chronic Refractory Primary Headaches: A Retrospective Case Series," The Journal of Headache and Pain, 2016, 8 pages.
Mavoori et al., "An Autonomous implantable computer for neural recording and stimulation in unrestrained primates," Journal of Neuroscience Methods, 2005, 7 pages.
McCreery et al., "Charge Density and Charge Per Phase as Cofactors in Neural Injury Induced by Electrical Stimulation," IEEE Transactions on Biomedical Engineering, vol. 37, No. 10, Oct. 1990, 6 pages.
McCreery et al., "Damage in Peripheral Nerve from Continuous Electrical Stimulation: Comparison of Two Stimulus Waveforms," Medical and Biological Engineering and Computing, Jan. 1992, 6 pages.
McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.
Medtronic—Spinal Cord Stimulation (SCS) Patient Management Guidelines for Clinicians, 1999, 114 pages.
Meyerson et al., Mechanisms of spinal cord stimulation in neuropathic pain, Neurological Research, vol. 22, Apr. 2000, 5 pages.
Miller, Jonathan, "Parameters of Spinal Cord Stimulation and Their Role in Electrical Charge Delivery: A Review," Neuromodulation: Technology at the Neural Interface, 2016, 12 pages.

Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The MED-EL SONATATI 100 Cochlear Implant: An evaluation of its safety in adults and children," Acta Oto-Laryngologica, vol. 131, No. 5, 2011, 8 pages.
Nevro—Leadership Through Innovation, J. P. Morgan 36th Annual Healthcare Conference, Jan. 8, 2018, 21 pages.
Nevro—Leadership Through Innovation, J. P. Morgan 36th Annual Healthcare Conference, Jan. 24, 2019, 2 pages.
NIDCD-NIH 2011, Cochlear Implant Brochure, http://www.nidcd.nih.gov/health/hearing/pages/coch.aspx, Jun. 29, 2012, 2 pages.
North et al., "Spinal Cord Stimulation With Interleaved Pulses: A Randomized, Controlled Trial," vol. 10, No. 4, 2007, 9 pages.
OHSIPP Summer Newsletter, The Official Newsletter for the Ohio Society of Interventional Pain Physicians, vol. 1 Ed. 2, Summer 2010, 8 pages.
Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.
Precision—Physician System Handbook, Advanced Bionic Corporation, Part 9055253-0001, 2005, 92 pages.
Precision—Physician Trail Kit Insert, Advanced Bionic Corporation, Part 9055258-0001, 2005, 2 pages.
Precision Spinal Cord Stimulation—Charging System Insert, Advanced Bionic Corporation, Part 9055074-0001, 2004, 2 pages.
Precision Spinal Cord Stimulation—Charging System, Advanced Bionic Corporation, Part 9055259-0001, 2004, 2 pages.
Precision Spinal Cord Stimulation—Patient System Handbook, Advanced Bionic Corporation, Part 9055072-0001, 2004, 93 pages.
Precision Spinal Cord Stimulation—Patient Trial Journal, Advanced Bionic Corporation, Part 9055260-0001, 2004, 10 pages.
Precision Spinal Cord Stimulation—Physician Implant Manual, Advanced Bionic Corporation, Part 9055255-0001, 2005, 70 pages.
Precision Spinal Cord Stimulation—Physician Implant Manual, Advanced Bionic Corporation, Part 9055100, 2004, 62 pages.
Precision Spinal Cord Stimulation—Physician Lead Manual, Advanced Bionic Corporation, Part No. 9055183-001, May 2004, 31 pages.
Precision Spinal Cord Stimulation—Physician Lead Manual, Advanced Bionic Corporation, Part 9055095, 2004, 62 pages.
Precision Spinal Cord Stimulation—Physician Lead Manual, Advanced Bionic Corporation, Part 9055256-0001, 2005, 56 pages.
Precision Spinal Cord Stimulation—Physician Trail Handbook, Advanced Bionic Corporation, Part 9055254-0001, 2005, 66 pages.
Precision Spinal Cord Stimulation—Physician Trail Kit Model SC-7005, Part 9055066-001, Advanced Bionic Corporation, 2004, 2 pages.
Precision Spinal Cord Stimulation—Remote Control Model SC-5200, Part 9055107-001, 2004, Advanced Bionic Corporation, 2 pages.
Precision Spinal Cord Stimulation—Remote Control Model SC-5210, Advanced Bionic Corporation, Part 9055257-001, 2005, 2 pages.
Precision Spinal Cord Stimulation System—Patient System Handbook, Advanced Bionic Corporation, Part No. 9055184-001, May 2004, 86 pages.
Precision Spinal Cord Stimulation System, Patient Trial Handbook, Part 9055078, 2004, 74 pages.
Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.
Pudenz et al., "Neural Stimulation: Clinical and Laboratory Experiences", Surg. Neurol, 39:235-242 (1993).
Rapcan et al., Clinical Study, "High-Frequency—Spinal Cord Stimulation," Indexed and Abstracted in Science Citation Index Expanded and in Journal Citation Reports, 2015, 3 pages.
Renew Neurostimulation System—Clinician's Manual—Advanced Neuromodulation Systems, Life Gets Better, 2000, 77 pages.
Rosenblueth et al., "The Blocking and Deblocking Effects of Alternating Currents on Nerve," Department of Physiology in Harvard Medical School, Nov. 1938, 13 pages.

(56) References Cited

OTHER PUBLICATIONS

Schulman et al., "Battery Powered BION FES Network," Proceedings of the 26th Annual Conference of the IEEE EMBS, San Francisco, CA., Sep. 1-5, 2004, 4 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Shealy et al., "Dorsal col. Electrohypalgesia," Jul. 1969, 8 pages.
Shelden et al., "Depolarization in the Treatment of Trigeminal Neuralgia," Evaluation of Compression and Electrical Methods, Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 6 pages.
Shelden et al., "Electrical stimulation of the nervous system," Surg. Neurol. vol. 4, No. 1, Jul. 1975, 6 pages.
Smet et al.,., "Successful Treatment of Low Back Pain with a Novel Neuromodulation Device," AZ Nikolaas, 12 pages.
Smet et al., Poster: "High-Frequency Spinal Cord Stimulation at 10 kHz after Failed Traditional Spinal Cord Stimulation," NANS, 2013, 1 page.
St. Jude Medical, "Clinician's Manual—Percutaneous Lead Kit, Models 3143, 3146, 3149, 3153, 3156, 3159, 3183, 3186, 3189," 2016, 24 pages.
Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.
Taylor et al., "The Cross Effectiveness of Spinal Cord Stimulation in the Treatment of Pain: A Systematic Review of the Literature," Journal of Pain and Symptom Management, vol. 27, No. 4., Apr. 2001, 9 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
Tiede et al., "Novel Spinal Cord Stimulation Parameters in Patients with Predominate Back Pain," Neuromodulation: Technology at the Neural Interface, 2013, 6 pages.
Van Buyten et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Buyten et al., "Pain Relief for Axial Back Pain Patients," INS Meeting Poster, 1 page.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System," NANS Poster, 2013, 1 page.
Von Korff et al., "Assessing Global Pain Severity by Self-Report in Clinical and Health Services Research," SPINE, vol. 25, No. 24, 2000, 12 pages.
Ward et al., "Electrical Stimulation Using Kilohertz-Frequency Alternating Current," Journal of the American Physical Therapy Association, vol. 89, No. 2, Feb. 2009, 12 pages.
Ward et al., "Variation in Motor Threshold with Frequency Using kHz Frequency Alternating Current," Muscle and Nerve, Oct. 2001, 9 pages.
Weinberg et al., "Increasing the oscillation frequency of strong magnetic fields above 101 kHz significantly raises peripheral nerve excitation thresholds," Medical Physics Letter, May 2012, 6 pages.
Wesselink et al., Analysis of Current Density and Related Parameters in Spinal Cord Stimulation, IEEE Transaction on Rehabilitation Engineering vol. 6, No. 2, Jun. 1998, 8 pages.
Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood et al., "Pulse Width Programming in Spinal Cord Stimulation: A Clinical Study," Pain Physician Journal, Jul./Aug. 2010, 16 pages.
Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
"The Need for Mechanism-Based Medicine in Neuromodulation," Neuromodulation: Technology at the Neural Interface, 2012, 7 pages.
Acticare.com website, http://web.archive.org/web/*/acticare.com, Internet Archive Way Back Machine, 2012, 22 pages.
Advanced Neuromodulation Systems, Compustim SCS Systems, Clinical Manual, 1997, 52 pages.
Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.
International Search Report and Written Opinion for International Patent Application No. PCT/US2017/014784, Applicant: Nevro Corp., dated May 1, 2017, 13 pages.
Amendment in Response to Ex Parte Office Action for U.S. Appl. No. 13/446,970, First Named Inventor: Konstantinos Alataris, dated Nov. 28, 2012, 14 pages.
Amendment in Response to Non-Final Office Action for U.S. Appl. No. 13/245,450, First Named Inventor: Konstantinos Alataris, filed Feb. 7, 2012, 15 pages.
Amendment in Response to Non-Final Office Action for U.S. Appl. No. 12/765,747, First Named Inventor: Konstantinos Alataris, dated Jan. 24, 2014, 21 pages.
Applicant-Initiated Interview Summary for U.S. Appl. No. 13/245,450, First Named Inventor: Konstantinos Alataris, dated Feb. 1, 2012, 2 pages.
Applicant-Initiated Interview Summary for U.S. Appl. No. 13/725,770, First Named Inventor: Konstantinos Alataris, dated Apr. 5, 2013, 3 pages.
Applicant-Initiated Interview Summary for U.S. Appl. No. 12/765,747, First Named Inventor: Konstantinos Alataris, dated Sep. 11, 2013, 3 pages.
Application Data Sheet for U.S. Appl. No. 13/446,970 (U.S. Pat. No. 8,359,102), First Named Inventor: Konstantinos Alataris, filed Apr. 13, 2012, 6 pages.
Augustinsson et al., "Spinal Cord Stimulation in Cardiovascular Disease," Functional Neurosurgery, vol. 6, No. 1, Jan. 1995, 10 pages.
Barolat et al., "Multifactorial Analysis of Epidural Spinal Cord Stimulation," Stereotactic and Functional Neurosurgery, 1991; 56: 77-103.
Barolat et al., "Spinal Cord Stimulation for Chronic Pain Management," Seminars in Neurosurgery, vol. 15, Nos. 2/3, 2004, 26 pages.
Barolat et al., "Surgical Management of Pain—Spinal Cord Stimulation: Equipment and Implantation Techniques," Chapter 41, Thieme Medical Publishers, New York, 2002, 11 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Bhadra et al., "High Frequency electrical conduction block of the pudendal nerve," Journal of Neural Engineering—Institute of Physics Publishing, 2006, 8 pages.
Bhadra et al., Stimulation of High-Frequency Sinusoidal Electrical Block of Mammalian Myelinated Axons, J Comput Neurosci, 22:313-326, 2007.

(56) References Cited

OTHER PUBLICATIONS

Bhadra MD, Niloy et al., "High-Frequency Electrical Conduction Block of Mammalian Peripheral Motor Nerve," Muscle and Nerve, Dec. 2005, 9 pages.
Boger et al., "Bladder Voiding by Combined High Frequency Electrical Pudendal Nerve Block and Sacral Root Stimulation," Neurourology and Urodynamics, 27, 2008, 5 pages.
Boston Scientific "Precision™ Spinal Cord Stimulator System Clinician Manual—Directions for Use," 2015, 74 pages.
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Bowman and McNeal, Response of Single Alpha Motoneurons to High-Frequency Pulse Trains, Appl. Neurophysiol. 49, p. 121-138, 1986, 10 pages.
Burton, Charles, "Dorsal Column Stimulation: Optimization of Application," Surgical Neurology, vol. 4, No. 1, Jul. 1975, 10 pages.
Butt et al., "Histological Findings Using Novel Stimulation Parameters in a Caprine Model," European Journal of Pain Supplements, 2011, 2 pages.
ClinicalTrials.gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.
Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.
Curriculum Vitae and Declaration of Dr. Ganesan Baranidharan on behalf of European Patent No. 2630984, 19 pages, 2016.
Curriculum Vitae and Declaration of Dr. Jonathan Miller on behalf of European Patent No. 2630984,42 pages, Oct. 25, 2016.
Curriculum Vitae and Declaration of Dr. Simon James Thomson on behalf of European Patent No. 2630984, Oct. 24, 2016, 13 pages.
Curriculum Vitae and Declaration of Prof. Bengt Linderoth on behalf of European Patent No. 2630984, Oct. 21, 2016, 6 pages.
Curriculum Vitae of Michael A. Moffitt for European Patent No. 2630984, 2015, 2 pages.
Declaration of Cameron C. McIntyre, Ph.D., May 6, 2015, 57 pages.
Declaration of Cameron C. McIntyre, Ph.D., May 6, 2015, 88 pages.
Declaration of M. Jason D. Rahn for European Patent No. 2243510, dated Feb. 2, 2017, 2 pages.
Declaration of M. Jason D. Rahn, Jan. 7, 2015, 7 pages.
Declaration of Prof. Bengt Linderoth for European Patent No. 2421600, dated Dec. 16, 2016 2 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
Ex Parte Office Action for U.S. Appl. No. 13/446,970, First Inventor Named: Konstantinos Alataris, dated Oct. 15, 2012, 9 pages.
Feeling vs. Function Poster, Mager and Associates Consulting, 2009, 1 page.
First Preliminary Amendment for U.S. Appl. No. 13/446,970, First Named Inventor: Konstantinos Alataris, dated May 18, 2012, 7 pages.
Grill, Warren et al., "Stimulus Waveforms for Selective Neural Stimulation," IEEE Engineering in Medicine and Biology, Jul./Aug. 1995, pp. 375-385.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
Huxely et al., "Excitation and Conduction in Nerve: Quantitative Analysis," Science, Sep. 11, 1964; 145: 1154-9.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
JMP Securities, "Nevro Corp. (NVRO) Initiating Coverage on Nevro Corp, with a Market Outperform Rating—Investment Highlights," Dec. 1, 2014, 42 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2015, 11 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.

(56) References Cited

OTHER PUBLICATIONS

Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mediati, R.D., "Mechanisms of Spinal Cord Stimulation," Florence, Oct. 2, 2002, 31 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.
Merriam Webster's Collegiate Dictionary, Tenth Edition, definition of "Implantable," 1995, 3 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Muller and Hunsperger, "Helvetica Physiologica et Pharmacologica Acta—Reversible Blockierung der Erregungsleitung im Nerven durch Mittelfrequenz—Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," Pain 80, 1999, 3 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx, 2016, 3 pages.
Nevro—Clinical Evidence www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview, www.nevro.com/English/Physicians/Physician-Overview/default.aspx, 2016, 5 pages.
Nevro—Senza System, http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Observations and Response to Notice of Oppositions filed by Medtronic Inc., and Boston Scientific for European Patent No. 2207587, mailed Aug. 26, 2016, 16 pages.
Nevro Response to Notice of Oppositions filed by Boston Scientific for European Patent No. 2421600, mailed Jul. 22, 2015, 16 pages.
Nevro Response to Notice of Oppositions filed by Medtronic and Boston Scientific for European Patent No. 2630984, mailed Dec. 7, 2015, 26 pages.
Nevro Response to Opposition of Division's Comments and Summons to Oral Proceedings for European Patent No. 2630984, mailed Oct. 25, 2016, 8 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro Written Submissions and Response to Notice of Oppositions filed by Medtronic Inc., and Boston Scientific for European Patent No. 2243510, mailed Aug. 28, 2015, 17 pages.
Nevro, PMA Approval Letter and Referenced Summary of Safety and Effectiveness Data (SSED) May 8, 2015, 60 pages.
Nevro's Response to Further Submission by Medtronic, Inc., and Boston Scientific Neuromodulation Corporation for European Patent No. 2243510, mailed Feb. 24, 2017, 9 pages.
Nevro's Response to Preliminary Opinion for Opposition by Medtronic, Inc., and Boston Scientific Neuromodulation Corporation for European Patent No. 2243510, dated Feb. 3, 2017, 36 pages.
Nevro's presentation of HF10 therapy on Nevro's website, http://www.nevro.com/English/Home/default.aspx, 2016, 2 pages.
Nevros Response to Opponent Submission of Declaration of Jonathan Miller in European Patent No. 2630984, mailed Nov. 18, 2016, 4 pages.
News Release Details, "Nevro Corp. Announces Pricing of Initial Public Offering," 2014, 1 page.
Non-Final Office Action for U.S. Appl. No. 12/765,747, First Named Inventor: Konstantinos Alataris, dated Jul. 25, 2013, 7 pages.
Non-Final Office Acton for U.S. Appl. No. 13/245,450, First Named Inventor: Konstantinos Alataris, dated Nov. 18, 2011, 11 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Failed Back Surgery Syndrome: 5-year Follow-Up after Spinal; Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," SPINE, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Notice of Allowance for U.S. Appl. No. 13/245,450, First Named Inventor: Konstantinos Alataris, dated Mar. 14, 2012, 8 pages.
Notice of Opposition to a European Patent for European Patent No. 2586488, Proprietor of the Patent: Nevro Corporation; Opponent: Medtronic, Inc., Mar. 15, 2017, 7 pages.
Notice of Opposition to a European Patent, Argument and Facts, for European Patent No. 2243510, Proprietor of the Patent: Nevro Corporation, Opponent: Medtronic, Jan. 8, 2015, 22 pages.
Notice of Opposition to a European Patent, Argument and Facts, and Annex for European Patent No. 2243510, Proprietor of the Patent: Nevro Corporation; Opponent: Boston Scientific Neuromodulation Corporation, Jan. 8, 2015, 28 pages.
Notice of Opposition to a European Patent, Argument and Facts, for European Patent No. 2207587, Proprietor of the Patent: Nevro Corporation; Opponent: Medtronic, Inc., Jan. 12, 2016, 22 pages.
Notice of Opposition to a European Patent, Argument and Facts, for European Patent No. 2207587, Proprietor of the Patent: Nevro Corporation; Opponent: Boston Scientific Neuromodulation Corporation, Jan. 8, 2016, 17 pages.

(56) References Cited

OTHER PUBLICATIONS

Notice of Opposition to a European Patent, Argument and Facts for European Patent No. 2630984, Proprietor of the Patent: Nevro Corporation; Opponent: Medtronic, Mar. 17, 2015, 17 pages.

Notice of Opposition to a European Patent, Argument and Facts, and Annex for European Patent No. 2630984, Proprietor of the Patent: Nevro Corporation; Opponent: Boston Scientific Neuromodulation Corporation, Mar. 17, 2015, 21 pages.

Notice of Opposition to a European Patent, Argument and Facts, and Annex for European Patent No. 2421600, Proprietor of the Patent: Nevro Corporation; Opponent: Boston Scientific Neuromodulation Corporation, Dec. 4, 2014, 22 pages.

Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.

Oakley et al., "Spinal Cord Stimulation in Axial Low Back Pain: Solving the Dilemma," Pain Medicine, vol. 7, No. S1, 2006, 6 pages.

Oakley, John C., "Spinal Cord Stimulation Mechanisms of Action,"SPINE vol. 27, No. 22, copyright 2002, 10 pages.

Opponent Boston Scientific: Response to Attend Oral Proceedings for European Patent No. 2630984, mailed Oct. 25, 2016, 21 pages.

Opponent Response to Patent Proprietor Comments to Declaration of Dr. Jonathan Miller for European Patent No. 2630984, mailed Nov. 22, 2016, 3 pages.

Opponents Boston Scientific Neuromodulation Corp.: Additional Observations in view of Oral Proceedings for European Patent No. 2243510, mailed Feb. 3, 2017, 8 pages.

Opponents Boston Scientific: Response to Summons to Attend Oral Proceedings for European Patent No. 2421600, mailed Jan. 2, 2017, 15 pages.

Opponents Medtronic, Inc.: Additional Observations in view of Oral Proceedings for European Patent No. 2243510, mailed Feb. 3, 2017, 10 pages.

Opponents Medtronic, Inc.: Response to Attend Oral Proceedings for European Patent No. 2630984, mailed Oct. 25, 2016, 26 pages.

Opponents Response to Patentee's (Nevro) Written Submissions for European Patent No. 2243510, mailed Feb. 22, 2016, 21 pages.

Palmer et al., "Transcutaneous electrical nerve stimulation and transcutaneous spinal electroanalgesia: A preliminary efficacy and mechanisms-based investigation," Physiotherapy, 95, 2009, 7 pages.

Partial European Search Report, European Application No. EP10160641, Applicant: Nevro Corporation, dated Aug. 30, 2010, 3 pages.

Patent Owner's Preliminary Response for Inter Partes Review for U.S. Pat. No. 8,359,102, Case No. IPR2015-01203, Petitioner: Boston Scientific Neuromodulation Corporation, Patent Owner: Nevro Corporation, dated Sep. 1, 2015, 70 pages.

Patent Owner's Preliminary Response for Inter Partes Review for U.S. Pat. No. 8,359,102, Case No. IPR2015-01204, Petitioner: Boston Scientific Neuromodulation Corporation, Patent Owner: Nevro Corporation, dated Sep. 1, 2015, 63 pages.

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.

Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, May 14, 2015, 45 pages.

Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, May 14, 2015, 67 pages.

Prausnitz et al., "The Effects of Electric Current Applied to Skin: A Review for Transdermal Drug Delivery," Advanced Drug Delivery Reviews 18, 1996, 31 pages.

Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.

Remedi Pain Relief—ENM (Electronic Nerve Modulation), https://web.archive.org/web/20050906181041/http://www.remediuk.com/trials.htm, 2005, 5 pages.

Resume of Jason D. Rahn, Jan. 7, 2015, 2 pages.

Robb et al., "Transcutaneous Electrical Nerve Stimulation vs. Transcutaneous Spinal Electroanalgesia for Chronic Pain Associated with ; Breast Cancer Treatments," Journal of Pain and Symptom Management, vol. 33, No. 4, Apr. 2007, 10 pages.

Royle, John., "Transcutaneous Spinal Electroanalgesia and Chronic Pain," Physiotherapy, vol. 86, No. 5, May 2000, 1 page.

Science Daily, "Chronic Pain Costs U.S. up to $635 billion, study shows," www.sciencedaily.com/releases/2012/09/120911091100.htm, Sep. 11, 2012, 2 pages.

Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.

Shealy MD, C. Norman et al., "Electrical Inhibition of Pain by Stimulation of the Dorsal Columns: Preliminary Clinical Report," Anesthesia and Analgesia Current Researches, vol. 446, No. 4, Jul.-Aug. 1967, 3 pages.

Simpson et al., "A Randomized, Double-Blind, Crossover Study of the Use of Transcutaneous Spinal Electroanalgesia in Patients with Pain from Chronic Critical Limb Ischemia," Journal of Pain and Symptom Management, vol. 28, No. 5, Nov. 2004, 6 pages.

Simpson, BA, "Spinal Cord Stimulation in 60 cases of Intractable Pain." Journal of Neurology, Neurosurgery and Psychiatry, 1991; 54 pp. 196-199.

Simpson, BA, "Spinal Cord Stimulation." British Journal of Neurosurgery, 1997, Feb. 11 (1), 5-11, 7 pages.

Sluijter et al., "The Effects of Pulsed Radiofrequency Fields Applied to the Dorsal Root Ganglion—A Preliminary Report," The Pain Clinic, vol. 11, No. 2, 1998, 12 pages.

Solomonow et al., "Control of Muscle Contractile Force through Indirect High-Frequency Stimulation," AM Journal of Physical Medicine, 1983, vol. 62, No. 3, pp. 71-82.

St. Jude Medical, "Eon Mini™ Rechargeable IPG," Apr. 29, 2013, 3 pages.

St. Jude Medical, "Individualized Therapy through Diverse Lead Options," 2008, 6 pages.

Stimwave, News Release: "Stimwave Receives FDA Approval for High Frequency IDE," http://stimwave.com/newsroom/latest-news, Jun. 9, 2015, 2 pages.

Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.

Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.

Tan et al., "Intensity Modulation: A Novel Approach to Percept Control in Spinal Cord Stimulation," Neuromodulation Technology at the Neural Interface, International Neuromodulation Society 2015, 6 pages.

Tanner, J.A., "Reversible blocking of nerve conduction by alternating-current; excitation," Nature, Aug. 18, 1962; 195: 712-3.

Tesfaye et al., "Electrical Spinal Cord Stimulation for Painful Diabetic Peripheral Neuropathy," The Lancet, vol. 348, Dec. 21-28, 1996, 4 pages.

Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.

Tollison et al., "Practical Pain Management Neurostimulation Techniques," Chapter 12, Lippincott Williams and Wilkins, Third Edition, 2002, 13 pages.

Towell et al., "High Frequency non-invasive stimulation over the spine: Effects on mood and mechanical pain tolerance in normal subjects," Behavioral Neurology, vol. 10, 1997, 6 pages.

(56) References Cited

OTHER PUBLICATIONS

Urban et al., "Percutaneous epidural stimulation of the spinal cord for relief of pain—Long Term Results," Journal of Neurosurgery, vol. 48, Mar. 1978, 7 pages.

Van Butyen et al., "High Frequency Spinal Cord Stimulation for the Treatment of Chronic Back Pain Patients: Results of a Prospective Multicenter European Clinical Study," Neuromodulation Technology at the ; Neural Interface, International Neuromodulation Society, 2012, 8 pages.

Van Den Honert et al. "Generation of Unidirectionally Propagated Action Potentials Nerve by Brief Stimuli" Science, vol. 26, pp. 1311-1312.

Van Den Honert, Mortimer JT, "A Technique for Collision Block of Peripheral Nerve: Frequency Dependence," MP-11 IEEE Trans. Biomed, Eng. 28: 379-382, 1981.

Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neuromodulation Society, 2014, 4 pages.

Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.

Webster's Third New International Dictionary of the English Language Unabridged, "Paresthesia," 1993, 3 pages.

Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

Woo MY, Campbell B. "Asynchronous Firing and Block of Peripheral Nerve Conduction by 20KC Alternating Current," Los Angeles Neuro Society, Jun. 1964; 87-94, 5 pages.

Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.

Medtronic—Neurological Division, Resume TL, Model 3986, Lead Kit for Spinal Cord Stimulation (SCS) and Peripheral Nerve Stimulation (PNS), Implant Manual, 1996, 27 pages.

Medtronic—Neurostimulation Systems: Expanding the Array of Pain Control Solutions, 1999, 6 pages.

Kulkarni et al., "A two-layered forward model of tissue for electrical impedance tomography," Physiol Meas., 30(6); pp. 1-24, Jun. 2009.

TREATMENT OF CONGESTIVE HEART FAILURE WITH ELECTRICAL STIMULATION, AND ASSOCIATED SYSTEMS AND METHODS

CROSS-REFERENCE TO RELATED APPLICATION

The present application is a division of U.S. patent Application Ser. No. 15/414,561 filed Jan. 24, 2017, which claims priority to U.S. Provisional Application No. 62/286,892, filed Jan. 25, 2016, and is incorporated herein by reference.

TECHNICAL FIELD

The present technology is directed generally to treatment of congestive heart failure with electrical stimulation, and associated systems and methods.

BACKGROUND

Congestive heart failure (CHF) is a chronic condition characterized by a reduction in contraction strength (e.g., contractility) of one or both of the main pumping chambers of the heart—the left and right ventricles. Reduced contractility of the ventricles reduces the volume of blood ejected by each ventricle per heart beat (e.g., stroke volume). When this occurs, the heart cannot pump blood with normal efficiency, and blood and other fluids begin to build up within the cardiovascular system and other parts of the body, such as the lungs, liver, abdomen, and lower extremities. In some cases of CHF, the myocardium (e.g., heart muscle tissue) becomes so weakened that the ventricles stretch or dilate, thereby damaging the Purkinje fibers located in the walls of the ventricles. The Purkinje fibers are responsible for carrying the contraction impulse to the myocardium of the ventricles, and thus damage to the Purkinje fibers by the dilated ventricles compromises the electrical conduction system of the heart and reduces the synchronization of contractility, further compromising the ejection fraction. Accordingly, there is a need for systems and methods for treating congestive heart failure.

DETAILED DESCRIPTION

Figure 1B:
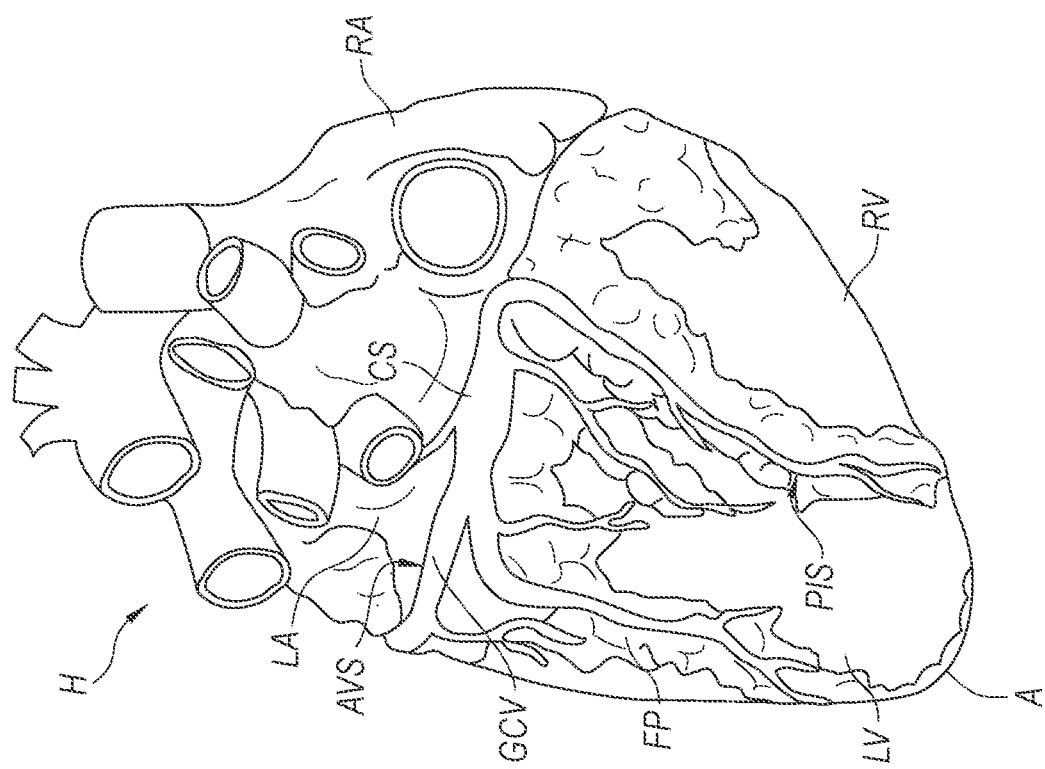
FIGS. 1A and 1B are anterior and posterior views, respectively, of a human heart.

The present technology is directed generally to systems for treating congestive heart failure (CHF), and in particular, to systems for treating CHF by improving contraction strength of the left and/or right ventricles via electrical stimulation. In one embodiment, the present technology includes a treatment system having an implantable signal generator and a signal delivery element configured to apply an electrical signal to a parasympathetic nerve innervating a portion of a patient's heart. The system includes one or more real-time feedback mechanisms for evaluating the efficacy of the applied signal and automatically adjusting the applied signal based on the efficacy. For example, in some embodiments the treatment system can automatically determine an ejection fraction of the patient's heart and adjust one or more parameters of the applied electrical signal based on the ejection fraction.

Definitions of selected terms are provided under heading 1.0 ("Definitions"). General aspects of the anatomical and physiological environment in which the disclosed technology operates are described below under heading 2.0 ("Introduction") with reference to FIGS. 1A and 1B. An overview of the treatment systems in which the disclosed technology operates is described below under heading 3.0 ("Overview") with reference to FIGS. 2A and 2B. Particular embodiments of the technology are described further under heading 4.0 ("Representative Embodiments") with reference to FIGS. 3-5. Additional embodiments are described under heading 5.0 ("Additional Embodiments).

1.0 Definitions

As used herein, "vagus nerve" refers to any of the following: portions of the left vagus nerve, the right vagus nerve, and/or the cervical vagus nerve, branches of the vagus nerve such as the superior cardiac nerve, superior cardiac branch, and inferior cardiac branch, and the vagus trunk. Similarly, stimulation of the vagus nerve is described herein by way of illustration and not limitation, and it is to be understood that in some embodiments of the present technology, other autonomic and/or parasympathetic nerves and/or parasympathetic tissue are stimulated, including sites where the vagus nerve innervates a target organ, vagal ganglia, nerves in the epicardial fat pads, a carotid artery, a jugular vein (e.g., an internal jugular vein), a carotid sinus, a coronary sinus, a vena cava vein, a pulmonary vein, and/or a right ventricle, for treatment of heart conditions or other conditions.

As used herein, "high frequency" or "HF" refers to a frequency of from about 1 kHz to about 100 kHz, or from about 1.2 kHz to about 100 kHz, or from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 kHz, or 1 kHz, 2 kHz, 3 kHz, 4 kHz, 5 kHz, 8 kHz, 9 kHz, 10 kHz, 11 kHz, 12 kHz, 15 kHz, 20 kHz, 50 kHz, or 100 kHz. As used herein, the term "about" refers to values within +/−10% of the stated value. Moreover, as used herein, "low frequency" or "LF" refers to a frequency less than about 1 kHz.

As used herein, "real-time" refers to within 10 seconds or less, within 5 seconds or less, within 3 seconds or less, within 2 seconds or less, within 1 second or less, within 0.5 seconds or less, within 0.25 seconds or less, and within 0.1 seconds or less.

2.0 Introduction

Figure 1A:
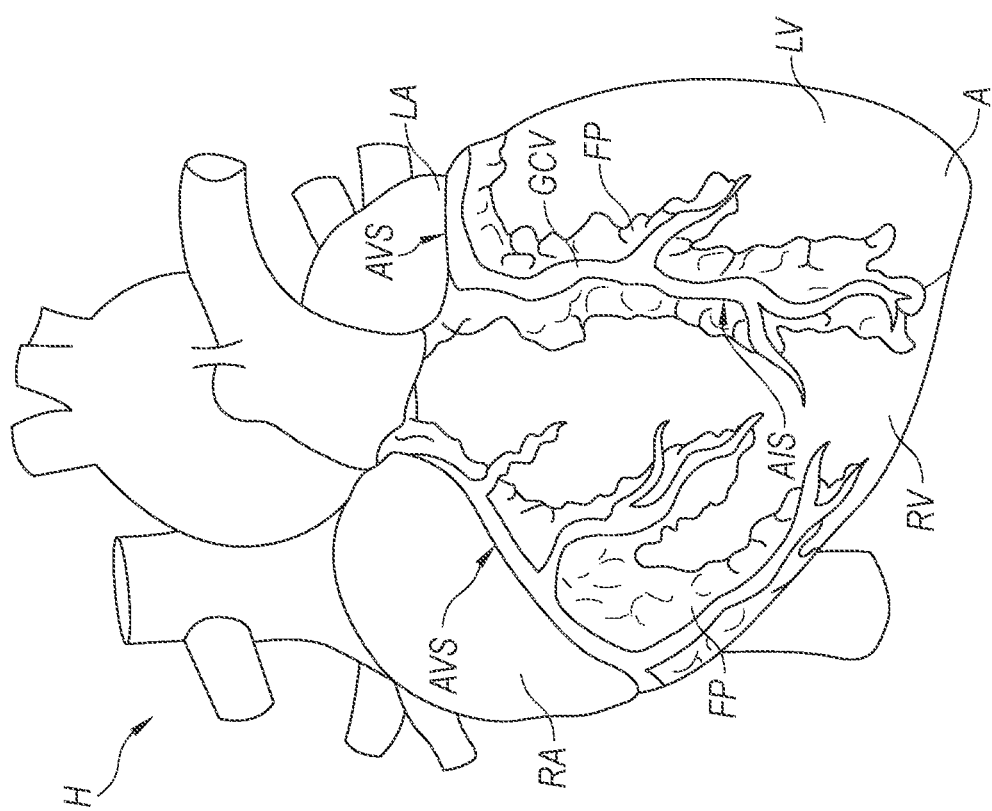

FIGS. 1A and 1B are anterior and posterior views, respectively, of a human heart H. As shown in FIGS. 1A and 1B, the heart H comprises four chambers, the right atrium RA, the left atrium LA, the right ventricle RV, and the left ventricle LV. The right and left atria RA, LA are separated from the right and left ventricles RV, LV by a groove known as the coronary or atrioventricular sulcus AVS. The anterior interventricular sulcus AIS and posterior interventricular sulcus PIS are grooves that separate the right and left ventricles RV, LV. Each of the atrioventricular sulcus AVS, the anterior interventricular sulcus AIS, and posterior interventricular sulcus PIS are surrounded by epicardial fat pads FP. The great cardiac vein GCV begins near the apex A of the heart and extends in a superior direction within the anterior interventricular sulcus AIS until eventually curving around the left side of the heart H within the atrioventricular sulcus AVS. A posterior portion of the great cardiac vein GCV empties into the coronary sinus CS, which is also positioned within the atrioventricular sulcus AVS.

3.0 Overview

Figure 2A:
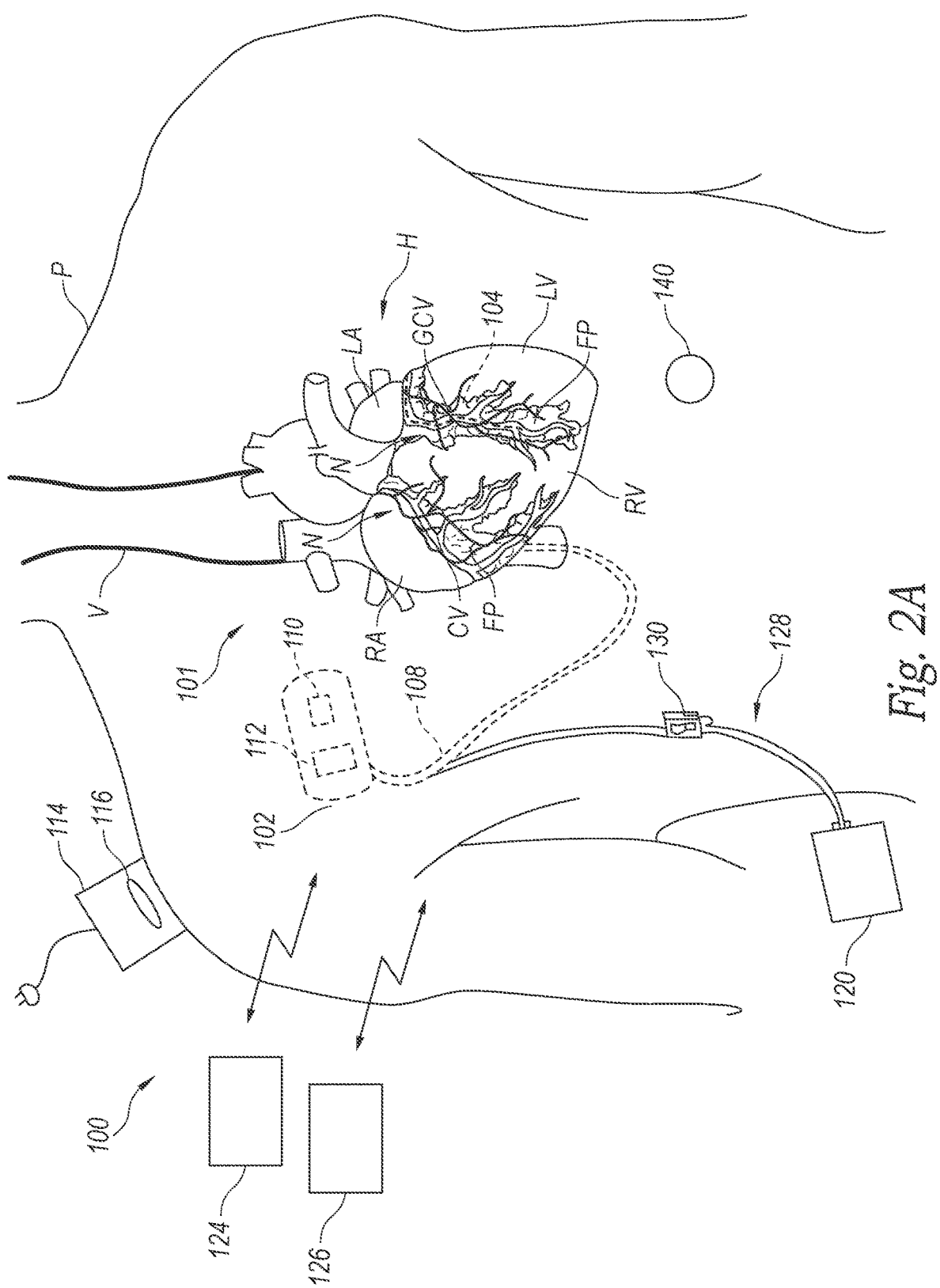
FIG. 2A is a partially schematic illustration of an implantable treatment system positioned to deliver electrical signals to the heart in accordance with several embodiments of the present technology.

FIG. 2A schematically illustrates a representative treatment system 100 for improving contractility of a patient's heart H, arranged relative to the general anatomy of a patient's heart H and chest region. As shown in FIG. 2A, parasympathetic innervation of the heart muscle is partially controlled by the vagus nerve V, which has branches that feed into one or more plexuses N located on, in and/or adjacent the epicardial fat pads FP. The treatment system 100 includes a signal delivery system 101 having a signal generator 102 (e.g., a pulse generator) and a signal delivery device or element 104. The signal generator 102 can be connected directly to the signal delivery element 104, or it can be coupled to the signal delivery element 104 via a signal link 108 (e.g., an extension). In one embodiment, signal generator 102 can be connected to signal delivery element 104 via wireless signal communication or wireless signal transmission. In some embodiments, the signal generator 102 may be implanted subcutaneously within a patient P, while in other embodiments signal generator 102 can be external to the patient. As shown in FIG. 2A, the signal delivery element 104 is configured to be positioned at or proximate to an epicardial fat pad FP, and to apply an electrical signal to the adjacent vagal plexus N. It is believed that high frequency modulation at or proximate the epicardial fat pads FP can modulate the parasympathetic nerve plexus(es) N located on or within the epicardial fat pads FP, thereby improving parasympathetic tone (e.g., the electrical activity of the parasympathetic nerve fibers) and ventricular contraction strength. As such, in one embodiment, the electrical signal applied to the vagal plexus N is a high frequency electrical signal (or high frequency therapy signal).

The signal generator 102 can transmit signals (e.g., electrical signals or therapy signals) to the signal delivery element 104 that up-regulate (e.g., stimulate or excite) and/or down-regulate (e.g., block or suppress) target nerves (e.g., local vagal nerves). As used herein, and unless otherwise noted, to "modulate," "stimulate," or provide "modulation" or "stimulation" to the target nerves refers generally to having either type of the foregoing effects on the target nerves. The signal generator 102 can include a machine-readable (e.g., computer-readable) medium containing instructions for generating and transmitting suitable therapy signals. The signal generator 102 and/or other elements of the treatment system 100 can include one or more processors 110, memories 112 and/or input/output devices. Accordingly, the process of providing electrical signals, detecting physiological parameters of the patient, determining ejection fraction, adjusting the modulation signal, and/or executing other associated functions can be performed by computer-executable instructions contained by computer-readable media located at the signal generator 102 and/or other system components. The signal generator 102 can include multiple portions, elements, and/or subsystems (e.g., for directing signals in accordance with multiple signal delivery parameters) housed in a single housing, as shown in FIG. 2A, or in multiple housings.

The signal delivery system 101 can include one or more sensing elements 140 for detecting one or more physiological parameters of the patient before, during, and/or after the application of electrical therapy signals. In some embodiments, one or more of the sensing elements 140 can be carried by the signal generator 102, the signal delivery element 104, and/or other implanted components of the system 101. In other embodiments, the sensing element(s) 140 can be an extracorporeal or implantable device separate from the signal generator 102 and/or signal delivery element 104. Representative sensing elements 140 include one or more of: an electrocardiogram ("ECG") unit, an impedance cardiography unit, a subcutaneous sensor, a ventricular sensor, an activity sensor (e.g., an accelerometer), a ventricular intracardiac sensor, an atrial intracardiac sensor, a temperature sensor, a flow rate sensor, a chemical sensor, a biosensor, an electrochemical sensor, a hemodynamic sensor, an optical sensor and/or other suitable sensing devices. Physiological parameters detected by the sensing element(s) 140 include heart rate, blood pressure, blood flow rate, activity level, ECG readings, impedance cardiography readings, ventricular and/or atrial pressure, and/or any correlates and/or derivatives of the foregoing parameters (e.g., raw data values, including voltages and/or other directly measured values).

In a representative embodiment, the signal delivery system 101 is configured to operate in either a "calibration mode" or an "active mode." In the calibration mode, the signal delivery system 101 is configured to apply a low frequency electrical signal (also referred to herein as the "LF calibration signal") via the signal delivery element 104 at the treatment site to determine a representative (e.g., maximum) signal amplitude that can be applied during subsequent treatment. In one embodiment, for example, the maximum signal amplitude is determined during the calibration mode to be the lower of: (1) the amplitude at which direct, immediate changes are observed to the heart rate, myocardial activation, or chamber sequencing, and (2) the amplitude which creates sensations which are perceived by the patient. In a particular embodiment, the signal delivery system 101 is also configured to apply a high frequency electrical signal (referred to herein as the "HF calibration signal") when in the calibration mode to validate the maximum signal amplitude identified by the LF calibration signal. In the active mode, the signal delivery system 101 is configured to apply a high frequency electrical signal (also referred to herein as the "HF treatment signal" or "HF therapy signal") at the treatment site to modulate the parasympathetic nerves proximate the treatment site. Parameters of the electrical signals applied by the signal delivery system 101 during calibration mode and/or active mode can be (1) automatically adjusted in response to a feedback mechanism and/or in accordance with a preset program (described in greater detail with reference to FIGS. 3-5), (2) manually adjusted in accordance with patient and/or practitioner inputs, and/or (3) automatically adjusted in a random or pseudorandom manner. "For example, a physician may find it beneficial to reduce the likelihood of the targeted nerves developing an adaptive, neuroplastic response that could diminish the efficacious effects of the applied signal over time. In such cases, an algorithm may be used to alter the applied amplitude of energy delivery in a pseudorandom manner. For example, the physician may set boundaries for the signal amplitude, such as a lower boundary of 0 mA and an upper boundary determined during calibration. Additionally, the physician may specify a schedule for varying the amplitude within the preset bounds, such as one amplitude change every N beats during the ventricular refractory period, M changes every beat during the ventricular refractory period, etc. Signal parameters include, for example, frequency, amplitude, pulse width, and duty cycle. It will be appreciated that in other embodiments, the signal delivery system 101 can be configured to operate in more than two modes.

In some embodiments, the signal generator 102 can obtain power to generate the therapy signals from an external power source 114. The external power source 114 can transmit power to the implanted signal generator 102 using electromagnetic induction (e.g., RF signals). For example, the external power source 114 can include an external coil 116 that communicates with a corresponding internal coil (not shown) within the implantable signal generator 102. The external power source 114 can be portable for ease of use.

In another embodiment, the signal generator 102 can obtain the power to generate therapy signals from an internal power source, in addition to or in lieu of the external power source 114. For example, the implanted signal generator 102 can include a non-rechargeable battery or a rechargeable battery to provide such power. When the internal power source includes a rechargeable battery, the external power source 114 can be used to recharge the battery. The external power source 114 can in turn be recharged from a suitable power source (e.g., conventional wall power).

During at least some procedures, an external programmer 120 (e.g., a trial modulator) can be coupled to the signal delivery element 104 during an initial procedure, prior to implanting the signal generator 102. For example, a practitioner (e.g., a physician and/or a company representative) can use the external programmer 120 in calibration mode to vary the signal parameters provided to the signal delivery element 104 in real-time, and select optimal or particularly efficacious signal parameters and/or signal delivery element 104 placement, as discussed in greater detail below with reference to FIG. 4. In a typical process, the practitioner uses a cable assembly 128 to temporarily connect the external programmer 120 to the signal delivery element 104. Whether calibrating the signal delivery system 101 or applying the HF treatment signal, the practitioner can test the efficacy of the signal delivery element 104 in an initial position and/or with initial signal parameters. The practitioner can then disconnect the cable assembly 128 (e.g., at a connector 130), reposition the signal delivery element 104, and reapply the electrical signal. This process can be performed iteratively until the practitioner confirms the desired therapy signal parameters and/or position for the signal delivery element 104 are clinically effective. Optionally, the practitioner can move the partially implanted signal delivery element 104 without disconnecting the cable assembly 128.

After a trial period with the external programmer 120, the practitioner can implant the implantable signal generator 102 within the patient P for longer term treatment. The signal delivery parameters provided by the signal generator 102 can still be updated after the signal generator 102 is implanted, via a wireless physician's programmer 124 (e.g., a physician's remote).

Figure 2B:
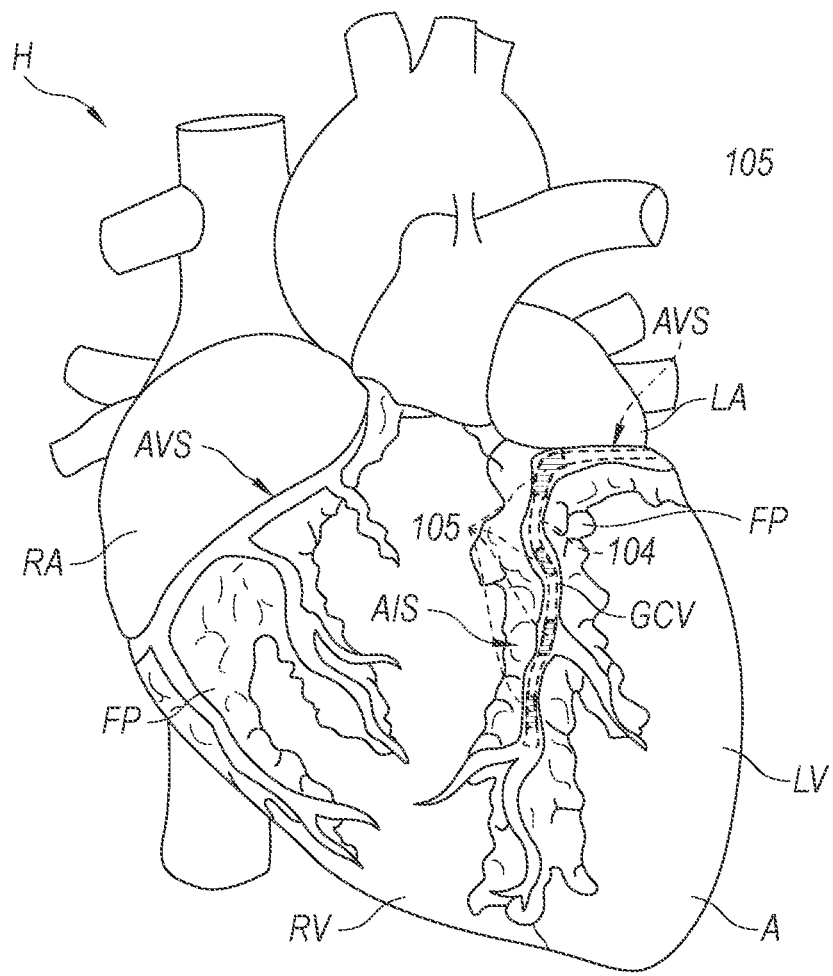
FIG. 2B is a partially schematic illustration of a portion of an implantable treatment system positioned to deliver electrical signals to the heart in accordance with several embodiments of the present technology.

FIG. 2B is a partially schematic illustration of the heart H along with a signal delivery element 104 implanted within the great cardiac vein GCV. The parasympathetic nerve fibers N depicted in FIG. 2A are not shown in FIG. 2B for purposes of clarity. In the representative embodiment, the signal delivery element 104 comprises a flexible, isodiametric lead or lead body that carries features or elements for delivering an electrical signal to the treatment site after implantation. As used herein, the terms "lead" and "lead body" include any of a number of suitable substrates and/or support members that carry devices for providing therapy signals to the patient. For example, the lead body can include one or more electrodes or electrical contacts 105 that direct electrical signals into the patient's tissue, such as to improve parasympathetic tone (e.g., parasympathetic electrical activity). In other embodiments, the signal delivery element 104 can include devices other than a lead body (e.g., a paddle) and/or other lead configurations (e.g., cardiac pacing leads, implantable cardioverter defibrillator (ICD) leads, cardiac resynchronization therapy (CRT) leads, left heart leads, epicardial leads, etc.) that also direct electrical signals and/or other types of signals to the patient. In a particular embodiment, the signal delivery system 101 (FIG. 2A) includes more than one signal delivery element 104 (e.g., two signal delivery elements 104, three signal delivery elements 104, four signal delivery elements 104, etc.), each configured to apply electrical signals at different locations and/or coordinate signal delivery to deliver a combined signal to the same (or generally the same) anatomical location.

As shown in FIG. 2B, the signal delivery element 104 can be positioned along at least a portion of the great cardiac vein GCV at or proximate the anterior interventricular sulcus AIS. In other embodiments, the signal delivery element 104 can be positioned at other cardiac locations at or proximate the epicardial fat pads FP. As used herein, "at or proximate the epicardial fat pads" refers to a position of the signal delivery element 104 that is in, on or otherwise in direct contact with a coronary vessel that is in direct contact with the targeted epicardial fat pad FP, and/or in direct contact with the adipocyte tissue of the targeted fat pad FP. For example, the signal delivery element 104 can be directly coupled to the fat pad FP tissue, positioned within a coronary artery, positioned within a coronary vein not in direct contact with the targeted epicardial fat pad FP and/or in direct contact with the adipocyte tissue of the targeted fat pad FP (e.g., the middle cardiac vein, the small cardiac vein, one or more anterior cardiac veins, the coronary sinus, etc.), positioned at an exterior portion of a coronary artery and/or coronary vein, positioned along at least a portion of the great cardiac vein GCV apart from the anterior interventricular sulcus AIS (e.g., at or proximate the atrioventricular sulcus AVS, etc.), and/or other suitable locations. In some embodiments, the signal delivery element 104 can be positioned on or within a coronary blood vessel such that the signal delivery element 104 spans more than one portion of the host blood vessel. For example, the signal delivery element 104 can be positioned such that (a) a first portion of the signal delivery element 104 coincides with at least a portion of the great cardiac vein GCV at or proximate the anterior interventricular sulcus AIS, and (b) a second portion of the signal delivery element 104 coincides with at least a portion of the great cardiac vein GCV at or proximate the atrioventricular sulcus AVS. In particular embodiments, the signal delivery element 104 can be coupled to and/or apply an electrical signal to more than one type of tissue (e.g., the adipose tissue of the fat pads FP and the neural tissue of the parasympathetic plexus N (FIG. 2A), the connective tissue of the blood vessel(s) and the neural tissue of the parasympathetic plexus N, etc.).

4.0 Representative Embodiments

Figure 3:
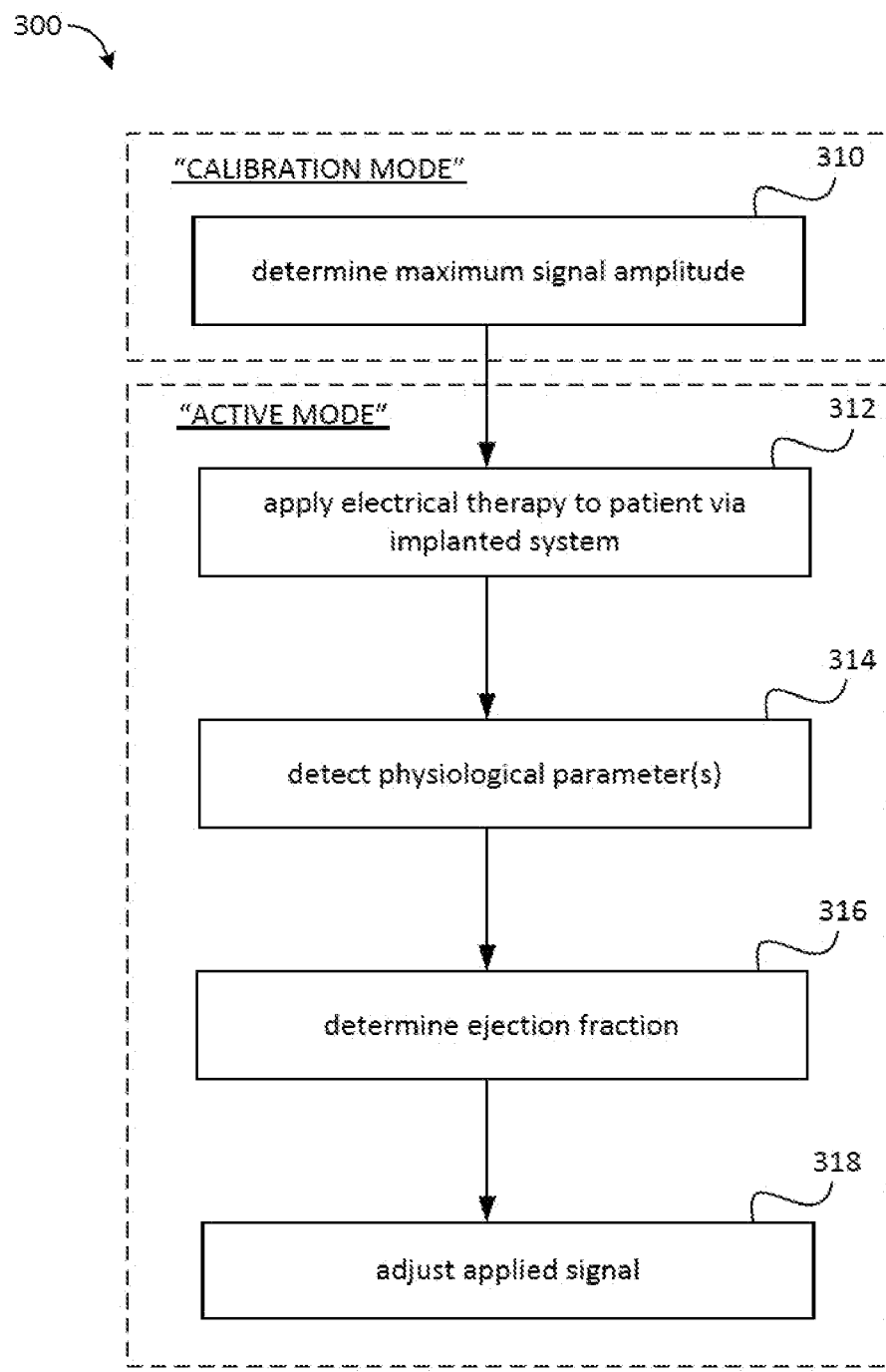
FIG. 3 is a flow diagram illustrating a method for treating congestive heart failure in accordance with an embodiment of the present technology.
Figure 4:
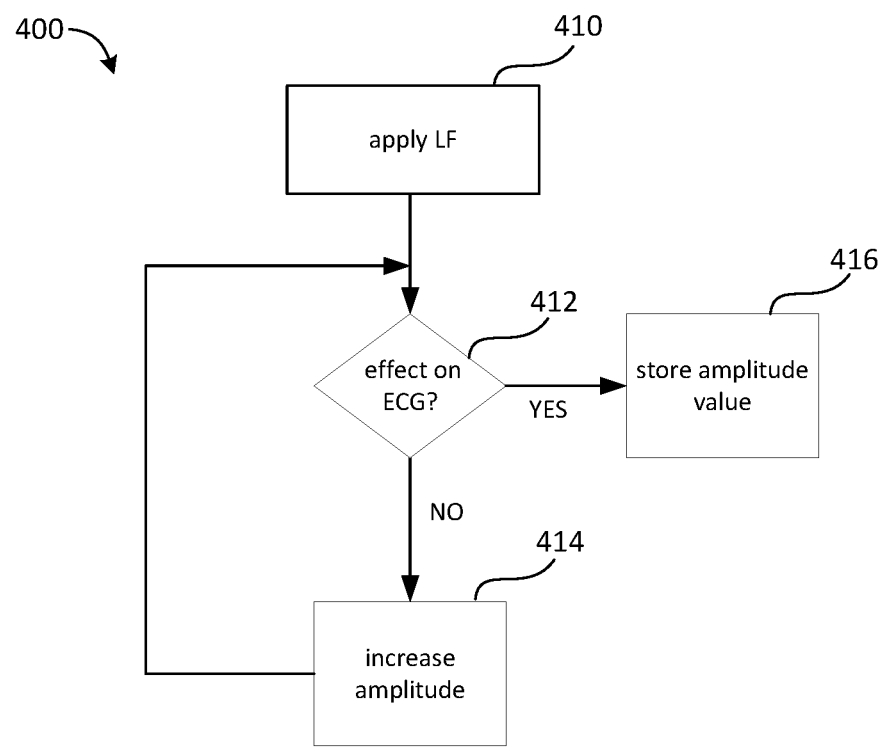
FIG. 4 is a flow diagram illustrating a method for determining a representative (e.g., maximum) treatment amplitude in accordance with an embodiment of the present technology.
Figure 5:
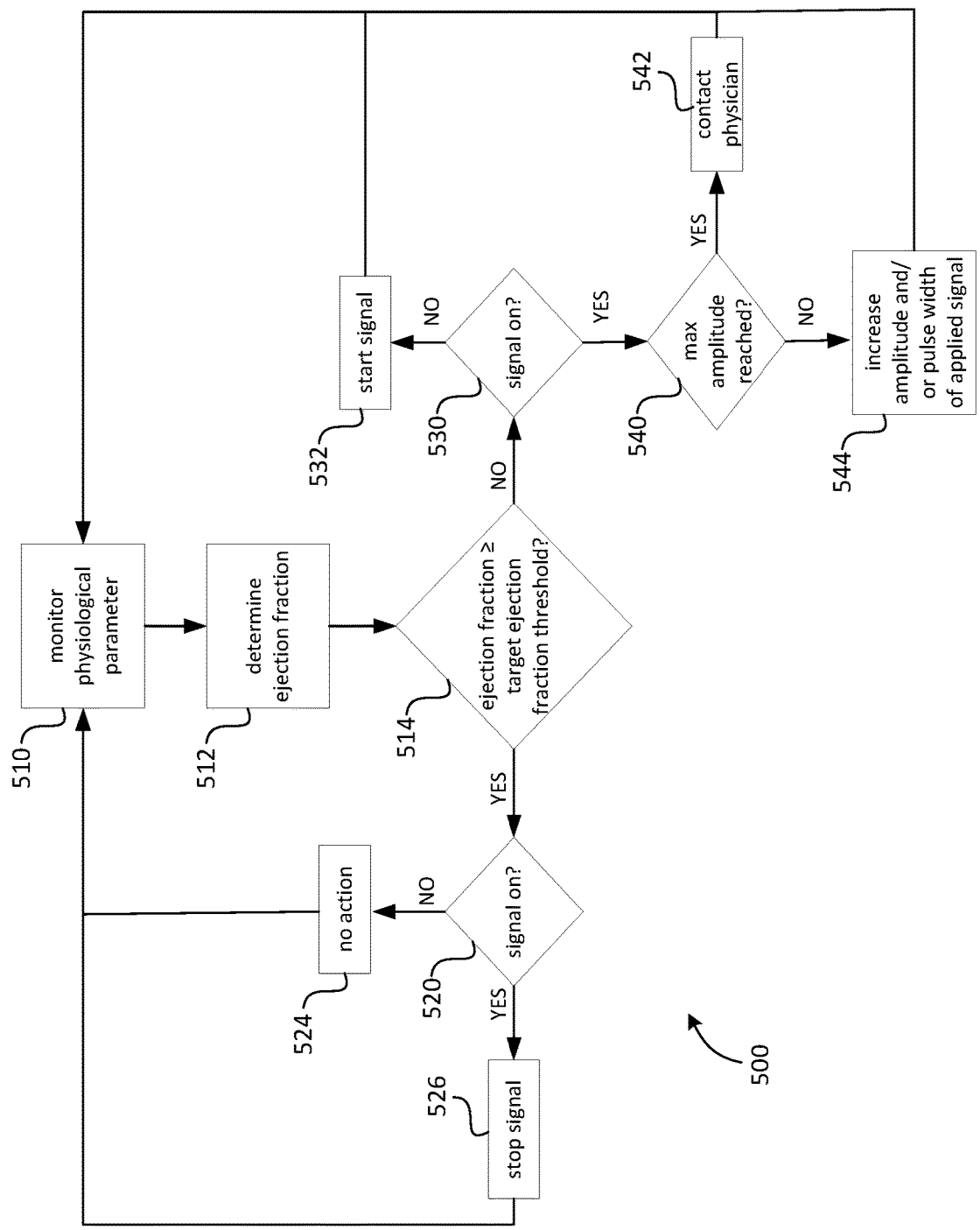
FIG. 5 is a flow diagram illustrating a method for adjusting a treatment signal in response to real-time ejection fraction feedback in accordance with an embodiment of the present technology.

FIGS. 3-5 illustrate a representative method for treating CHF and/or improving cardiac contractility utilizing the treatment system 100 described above with reference to FIGS. 2A and 2B. FIG. 3 illustrates an overall process 300 in accordance with a particular embodiment of the disclosure. The overall process 300 includes determining a representative (e.g., maximum) treatment amplitude (process portion 310), applying an HF treatment signal to a patient via the signal delivery system 101 (FIG. 2A) (process portion 312), and automatically detecting one or more physiological parameters of the patient (process portion 314). The process 300 can further include automatically determining an ejection fraction of the patient's heart based on the detected physiological parameter (process portion 316) and, based on the determined ejection fraction, automatically adjusting one or more parameters of the HF treatment signal (process portion 318). FIGS. 4 and 5 describe further aspects of particular embodiments of the foregoing process.

FIG. 4 is a block diagram 400 illustrating a representative method for determining a representative (e.g., maximum) signal amplitude prior to modulating the nerves to prevent unwanted effects on the electrical conduction system of the heart (e.g., tachycardia, bradycardia, etc.) during treatment. In block 410, with the signal delivery system 101 (FIG. 2A) in calibration mode, the practitioner applies the calibration signal to the treatment site. In the embodiment shown, an LF calibration signal is applied. In an alternative embodiment, however, a HF calibration signal may be applied. In a particular embodiment, the LF calibration signal can have a frequency of from about 0.1 to about 2.5 Hz, and in some embodiments, less than 1 Hz. In some embodiments the LF calibration signal can have a pulse width greater than 600 microseconds, and in certain embodiments, of from about 100 microseconds to about 2.5 milliseconds. During application of the LF calibration signal, the practitioner and/or system processor 110 can monitor an ECG of the patient for any changes (e.g., timing changes in the PQRST wave) while increasing the amplitude of the applied signal from a starting amplitude value (e.g., starting at an amplitude of 0.1 mA and increasing the amplitude in increments; for example of 0.1 mA, 0.2 mA, 0.5 mA, or 1.0 mA). As indicated by blocks 412 and 414, as long as no cardiac effect is detected on the ECG, the practitioner and/or processor 110 (FIG. 2A) can continue to increase the amplitude of the LF calibration signal. As indicated by blocks 412 and 416, if at any point the practitioner and/or system processor 110 detects a change in the ECG, the amplitude of applied signal can cease to increase and the amplitude at which the change in the ECG was detected is automatically stored in system memory 112 (FIG. 2A) (e.g., within the signal generator 102 (FIG. 2A) and/or the external programmer 120 (FIG. 2A)) and/or manually entered by the practitioner.

In a particular embodiment, the signal delivery system 101 (FIG. 2A) is optionally configured to determine a representative (e.g., maximum) HF signal amplitude by applying an HF calibration signal to the treatment site and monitoring the patient's ECG while increasing the HF calibration signal's amplitude from a starting amplitude value. In some embodiments, the HF calibration signal has a pulse width less than or equal to 1/(2*(the frequency of the HF calibration signal), and in a particular embodiment, of from about 100 nanoseconds to less than or equal to 1/(2*(the frequency of the HF calibration signal). In other embodiments, the signal can have other suitable pulse widths. Similar to the LF calibration process 400, as long as no cardiac effect is detected on the ECG, the practitioner and/or processor 110 (FIG. 2A) continues to increase the amplitude of the HF calibration signal. If at any point the practitioner and/or system processor 110 detects a change in the ECG, the amplitude of applied HF calibration signal can cease to increase and the amplitude at which the change in the ECG was detected is automatically stored in system memory 112 (FIG. 2A) (e.g., within the signal generator 102 (FIG. 2A) and/or the external programmer 120 (FIG. 2A)) and/or manually input by the practitioner. Although it is expected that the electrical energy required to trigger cardiac activity at the LF calibration signal will be much lower than the electrical energy required at the HF calibration signal, it can be advantageous in some procedures to determine the maximum treatment amplitude with the HF calibration signal to validate the maximum treatment signal amplitude determined using the LF calibration signal. Moreover, in some instances the physician may use the HF calibration signal to set the upper and lower bounds of the HF treatment signal amplitude. For example, in some embodiments the upper bound of the HF treatment signal amplitude can be set to the representative LF calibration signal amplitude plus 0.5*(the representative HF calibration signal amplitude minus the representative LF calibration signal amplitude). In yet other embodiments, the physician may set the HF treatment signal amplitude upper bound to 0.9*(the LF calibration signal amplitude).

Once the maximum treatment signal amplitude has been determined, the system 101 (FIG. 2A) can be put in active mode (as indicated in FIG. 3). In active mode, the signal delivery system 101 is configured to apply a therapy signal to the treatment site. Without being bound by theory, HF signals are believed to have significantly improved therapeutic effects when compared to LF signals in modulating the vagal nerve at the heart because it is believed that the LF signal parameters required for an LF signal to therapeutically modulate the vagal nerve would also necessarily activate the myocardium and induce unwanted cardiac effects (e.g., tachycardia, bradycardia, etc.). In some embodiments, an HF treatment signal is applied and can have a starting amplitude of about 90% of the maximum signal amplitude (determined during calibration mode). In a representative embodiment, the HF treatment signal is a pulse train with a duty-cycle from about 1% on to about 90% on (e.g., 10% or about 10% on, 25% or about 25% on, 50% or about 50% on, 70% or about 70% on, etc.). The HF treatment signal can have a pulse width of from about 1 us to about 80 µs, and in some embodiments, of from about 20 us to about 60 µs (e.g., 30 µs, 37 µs, 42 µs, etc.). The HF treatment signal can also have an interpulse width of from about 0 us to about 50 µs, or of from about 10 us to about 40 µs. In other embodiments, the HF treatment signal can be any charge-balanced, alternating-current waveform, such as a bi-phasic waveform, a sine waveform, a square waveform, a triangular waveform, a rectangular waveform, etc. In yet other embodiments, the treatment signal is not pulsed and instead is delivered continuously. In such embodiments, charge balancing can be achieved via active recharge on a pulse-by-pulse basis. As discussed in greater detail below with reference to FIG. 5, the signal delivery system 101 can control the timing of the application of the HF treatment signal based on one or more feedback mechanisms and/or preset programs (e.g., based on time of day). For example, the system 101 can be programmed to deliver the HF treatment signal for seconds, minutes, hours, days, weeks, and/or months at a time. In these and other embodiments, the signal delivery system 101 can be configured to apply the HF treatment signal continuously while implanted.

Application of the HF treatment signal at the treatment site (e.g., at or proximate an epicardial fat pad) is expected to modulate one or more vagal nerves at or proximate to the treatment site, thereby improving parasympathetic tone and cardiac contractility. One way to assess contractility and/or the efficacy of the treatment is by measuring ejection fraction, or the percentage of blood pumped out of the heart during each beat. An increase in ejection fraction indicates improved contractility and, likewise, a decrease in ejection fraction indicates reduced contractility. Under resting conditions, healthy adults have an average ejection fraction between 50% and 75%. Below 50%, the patient may experience a variety of symptoms, including shortness of breath, inability to exercise, swelling of the feet and lower legs, fatigue, weakness, and rapid or irregular heartbeat. Below 30%, the patient's quality of life is minimal and death may be imminent.

When the signal delivery system 101 (FIG. 2A) is in active mode—whether applying the treatment signal or not—the treatment system 100 and/or signal delivery system 101 can be configured to continuously or intermittently monitor one or more physiological parameters of the patient via the one or more sensing elements 140 (FIG. 2A). In a representative embodiment, the sensing element(s) 140 are positioned and/or otherwise configured to sense one or more physiological parameters that, when analyzed together by the processor 110, provide a reliable, real-time estimate of ejection fraction that can be used to adjust the treatment signal. Such physiological parameters include systolic pressure, diastolic pressure, interatrial pressure, flow rate, arterial pressure, heart rate, ventricular volume, ventricular impedance, blood oxygen saturation, and/or any derivative of the foregoing. In a particular embodiment, for example, the system 101 includes an algorithm that continuously and/or iteratively monitors ventricular impedance and heart rate and, based on those parameters, determines a change in ventricular volume over time (dVV/dt). In another embodiment, the system 101 includes one or more transducers configured for echocardiographic signaling. For example, in some embodiments the signal delivery element 104 (FIG. 2A) includes an array of piezoelectric transducers configured to emit sound waves towards one or more chambers of the heart, detect the reflected sound waves, and convert the reflected sound waves into a signal for storage and/or processing by the processor 110 (FIG. 2A). In these and other embodiments, the system 101 can include one or more transducers separate from the signal delivery element 104 and configured to be positioned at or near the heart and/or other internal and/or external anatomical locations. It will be appreciated that the system 101 can include multiple algorithms for determining and/or estimating ejection fraction. For example, in a particular embodiment, the system 101 can include an algorithm that estimates ejection fraction by monitoring changes in contraction velocity (e.g., via an accelerometer at the lead).

FIG. 5 is a block diagram 500 illustrating a method for adjusting the timing and/or one or more other parameters of the treatment signal in response to real-time ejection fraction feedback. As indicated at blocks 510 and 512, when the signal delivery system 101 is in active mode, the sensing element(s) 140 (FIG. 2A) continuously or intermittently communicate the sensed parameter values to the system processor 110 (FIG. 2A) and/or memory 112 (FIG. 2A). The processor 110 can determine an ejection fraction measurement (also referred to herein as the "EF measurement") based on the sensed parameters (block 512). The EF measurement can be an instantaneous ejection fraction value or set of values, an average ejection fraction value over a period of time, and/or any derivative or correlate of either of the foregoing, such as a change in ejection fraction over time (dEF/dt) (or lack thereof) and a rate of change of ejection fraction EF over time ($d^2EF/dt^2$) (or lack thereof).

In block 514, the processor 110 (FIG. 2A) compares the EF measurement with a target ejection fraction threshold (also referred to herein as "target EF threshold"). The target EF threshold is a standardized or patient-specific ejection fraction metric that represents an improvement in ejection fraction relative to the patient's ejection fraction prior to treatment. The target EF threshold can be a single value or range of values, and can be determined prior to treatment and/or adjusted during treatment. Similar to the EF measurement, the target EF threshold can be an instantaneous ejection fraction value or set of values, an average ejection fraction value over a period of time, and/or any derivative of either of the foregoing, such as a change in ejection fraction over time (dEF/dt) (or lack thereof) and a rate of change of ejection fraction over time ($d^2EF/dt^2$) (or lack thereof). Moreover, on some embodiments the system 101 (FIG. 2A) may take into account multiple different EF measurements and/or multiple different target EF thresholds at decision block 514, and/or require more than one comparison before choosing a course of action.

As indicated by block 530, if the EF measurement is less than the target EF threshold, the processor 110 (FIG. 2A) will take one of two actions based on whether the signal delivery system 101 (FIG. 2A) is currently applying a treatment signal. If the EF measurement is less than the target EF threshold and the signal delivery system 101 is presently applying the treatment signal, one or more parameters of the treatment signal may not be sufficient to modulate the parasympathetic nerves. In such a scenario (indicated by block 544), the processor 110 can adjust one or more signal parameters (e.g., increase the treatment signal amplitude and/or the pulse width of the treatment signal) to increase the intensity of the treatment signal. As indicated by blocks 540 and 542, the processor 110 will not increase the treatment signal magnitude if the maximum treatment signal amplitude has already been reached. Alternatively, if the EF measurement is less than the target EF threshold and the signal delivery system 101 is not presently applying the treatment signal, then the processor 110 can initiate application of the treatment signal.

As indicated by block 520, if the EF measurement is greater than or equal to the target EF threshold, the processor 110 (FIG. 2A) will take one of two actions based on whether the signal delivery system 101 (FIG. 2A) is currently applying a treatment signal. If the EF measurement is greater than the target EF threshold and the signal delivery system 101 is presently applying the treatment signal, it may be beneficial to cease applying the treatment signal (indicated by block 526) but continue monitoring ejection fraction should the EF measurement fall below the target EF threshold. Alternatively, if the EF measurement is greater than the target EF threshold and the signal delivery system 101 is not presently applying the treatment signal, then the processor 110 can continue to not apply the treatment signal (indicated by block 524) but monitor ejection fraction should the EF measurement fall below the target EF threshold.

It will be appreciated that in any of the above embodiments, the signal delivery system 101 (FIG. 2A) can measure other parameters (in addition to ejection fraction) and can additionally or alternatively adjust the timing and/or signal parameters of the treatment signal in response to such other measurements and/or any parameter sensed by the sensing elements 140. For example, the signal delivery system 101 can be configured to detect an average heart rate outside of a target heart rate threshold, and, for example, if the detected heart rate is greater than the target heart rate threshold while the treatment signal is being applied, the processor 110 can decrease the pulse width and/or increase the amplitude of the treatment signal in order to increase the parasympathetic tone.

5.0 Additional Embodiments

Embodiments of the presently disclosed technology are described in the following examples. A method for treating congestive heart failure in a patient in accordance with one example includes applying an electrical signal to the patient via a treatment system that includes a signal delivery element in electrical communication with the patient's vagus nerve at a portion of the vagus nerve located at or proximate to the anterior interventricular junction of the patient's heart, with the electrical signal having a frequency of from about 1 kHz to about 100 kHz. The method further includes automatically detecting at least one physiological parameter of the patient, automatically determining at least one of an ejection fraction of the patient's heart and a correlate of the ejection fraction based on the detected parameter, and automatically adjusting the applied signal based on the determined ejection fraction. In some embodiments of the method, automatically adjusting the applied signal includes stopping the application of the applied signal in response to detecting an ejection fraction greater than or equal to a target ejection fraction threshold. In these and other embodiments, automatically adjusting the applied signal includes increasing at least one of an amplitude of the applied signal and a pulse width of the applied signal in response to detecting an ejection fraction less than a target ejection fraction threshold and/or automatically adjusting the applied signal includes decreasing at least one of an amplitude of the applied signal and a pulse width of the applied signal in response to detecting an ejection fraction greater than or equal to a target ejection fraction threshold. In some embodiments, automatically detecting a physiological parameter includes automatically detecting the patient's heart rate, and automatically adjusting the applied signal includes increasing at least one of an amplitude of the applied signal and a pulse width of the applied signal in response to the increase in the patient's heart rate. Further, in at least some embodiments of the method, applying the electrical signal occurs at a first time and automatically adjusting the applied signal includes applying the electrical signal at a second time in response to detecting an ejection fraction less than the target ejection fraction threshold. In a particular embodiment, applying the electrical signal includes applying the signal to the patient via a lead positioned at or proximate to the atrial-ventricular fat pads of the patient's heart. In certain embodiments of the method, applying the electrical signal includes applying the signal with a pulse width less than or equal to 1/(2×the frequency of the signal). In further embodiments, the treatment system includes an implantable treatment system. In yet further embodiments, the at least one detected physiological parameter includes at least one of the patient's heart rate, the patient's blood pressure, and the patient's blood flow rate.

A method for treating congestive heart failure in a patient in accordance with another representative example includes applying an electrical signal having a frequency of from about 1 kHz to about 100 kHz to an epicardial fat pad of the patient's heart, automatically monitoring an ejection fraction of the patient, automatically comparing the monitored ejection fraction value to a predetermined threshold, and based on the comparison, automatically adjusting the applied signal. In some embodiments of the method, automatically adjusting the applied signal includes stopping the application of the applied signal in response to detecting an ejection fraction greater than or equal to a target ejection fraction threshold. In these and other embodiments, automatically adjusting the applied signal includes increasing at least one of an amplitude of the applied signal and a pulse width of the applied signal in response to detecting an ejection fraction less than a target ejection fraction threshold and/or automatically adjusting the applied signal includes decreasing at least one of an amplitude of the applied signal and a pulse width of the applied signal in response to detecting an ejection fraction greater than or equal to a target ejection fraction threshold. In a particular embodiment of the method, applying the electrical signal occurs at a first time, and wherein automatically adjusting the applied signal includes applying the electrical signal at a second time in response to detecting an ejection fraction less than the target ejection fraction threshold.

Still a further representative example of a system for treating congestive heart failure in a patient in accordance with the present technology includes an electrical signal generator having a computer readable storage medium, and an implantable signal delivery element coupled to the signal generator. The signal generator can be configured to be positioned proximate an epicardial fat pad of the patient and apply an electrical signal having a frequency of from about 1 kHz to about 100 kHz to neural tissue proximate and/or within the epicardial fat pad. In some embodiments of the system, the computer-readable storage medium has instructions that, when executed, determine an ejection fraction of the patient's heart in real-time and adjust the signal applied by the signal delivery element in response to the determined ejection fraction. In a particular embodiment, the system further comprises a sensor in communication with the computer-readable storage medium. In at least some of such embodiments, the sensor is configured to detect a physiological parameter of the patient, and the instructions, when executed, calculate the ejection fraction based on the physiological parameter. In a certain embodiment of the system, the signal generator is an implantable signal generator. In further embodiments of the system, the instructions, when executed, and in response to a determined ejection fraction greater than or equal to a predetermined target threshold, cease to apply the electrical signal. In these and other embodiments, the instructions, when executed, and in response to a determined ejection fraction less than or equal to a predetermined target threshold, start application of the electrical signal and/or in response to a determined ejection fraction less than or equal to a predetermined target threshold, increase at least one of an amplitude or a pulse width of the electrical signal. In a representative embodiment of the system, the signal delivery element is configured to be positioned within a coronary blood vessel of the patient.

From the foregoing, it will be appreciated that specific embodiments of the disclosed technology have been described herein for purposes of illustration, but that various modifications may be made without deviating from the technology. For example, in some embodiments the system 101 (FIG. 2A) can be configured to deliver pacing signals to the heart. In such embodiments, for example, the system 101 can include a single signal generator configured to transmit pacing signals and modulating signals, or the system 101 can include a modulating signal generator (e.g., signal generator 102 (FIG. 2A) and a separate pacing signal generator (e.g., external or implantable). In those embodiments having a single signal generator configured to transmit pacing and modulating signals, the system 101 can include one or more signal delivery element(s) configured to deliver pacing signals, modulating signals, or both.

Certain aspects of the technology described in the context of particular embodiments may be combined or eliminated in other embodiments. For example, in some embodiments the signal generator 102 (FIG. 2A) is configured to only transmit LF or HF signals in calibration mode, and in other embodiments the signal generator 102 may not include a calibration mode. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

To the extent any materials incorporated herein by reference conflict with the present disclosure, the present disclosure controls.

We claim:

1. A method for treating congestive heart failure in a patient, comprising:
    applying an electrical signal to the patient via a treatment system to excite neural tissue proximate and/or within an epicardial fat pad of the patient's heart wherein the treatment system includes a signal delivery element positioned at the epicardial fat pad of the patient's heart, the electrical signal having a frequency in a range of from about 1 kHz to about 100 kHz;
    automatically detecting at least one physiological parameter of the patient via one or more sensing elements;
    based on the detected parameter, automatically determining an ejection fraction indicator that is at least one of an ejection fraction of the patient's heart and a correlate of the ejection fraction; and
    automatically adjusting the applied signal based on the determined ejection fraction indicator.

2. The method of claim 1 wherein automatically adjusting the applied signal includes stopping the application of the applied signal in response to detecting an ejection fraction indicator greater than or equal to a target ejection fraction threshold.

3. The method of claim 1 wherein applying the electrical signal occurs at a first time, and wherein automatically adjusting the applied signal includes applying the electrical signal at a second time in response to detecting an ejection fraction indicator less than the target ejection fraction threshold.

4. The method of claim 1 wherein automatically adjusting the applied signal includes increasing at least one of an amplitude of the applied signal and a pulse width of the applied signal in response to detecting an ejection fraction indicator less than a target ejection fraction threshold.

5. The method of claim 1 wherein automatically adjusting the applied signal includes decreasing at least one of an amplitude of the applied signal and a pulse width of the applied signal in response to detecting an ejection fraction indicator greater than or equal to a target ejection fraction threshold.

6. The method of claim 1 wherein:
    automatically detecting a physiological parameter includes automatically detecting the patient's heart rate; and
    automatically adjusting the applied signal includes increasing at least one of an amplitude of the applied signal and a pulse width of the applied signal in response to the increase in the patient's heart rate.

7. The method of claim 1 wherein applying the electrical signal includes applying the signal to the patient via a lead positioned at or proximate to the atrial-ventricular fat pads of the patient's heart.

8. The method of claim 1 wherein applying the electrical signal includes applying the signal with a pulse width less than or equal to 1/(2×the frequency of the signal).

9. The method of claim 1 wherein the treatment system includes an implantable treatment system.

10. The method of claim 1 wherein the at least one detected physiological parameter includes at least one of the patient's heart rate, the patient's blood pressure, and the patient's blood flow rate.

11. A method for treating congestive heart failure in a patient, comprising:
    applying an electrical signal to the patient via a treatment system to increase a contraction strength of a left ventricle and/or a right ventricle of the patient's heart, wherein the treatment system includes a signal delivery element positioned at an epicardial fat pad of the patient's heart, and wherein the electrical signal has a frequency in a range of from about 1 kHz to about 100 kHz;
    automatically detecting at least one physiological parameter of the patient via one or more sensing elements;
    based on the detected parameter, automatically determining an ejection fraction indicator that is at least one of an ejection fraction of the patient's heart and a correlate of the ejection fraction; and
    automatically adjusting the applied signal based on the determined ejection fraction indicator.

12. The method of claim 11 wherein applying the electric signal increases the contraction strength of the left ventricle.

13. The method of claim 11 wherein applying the electric signal increases the contraction strength of the right ventricle.

14. The method of claim 11 wherein automatically adjusting the applied signal includes stopping the application of the applied signal in response to detecting an ejection fraction indicator greater than or equal to a target ejection fraction threshold.

15. The method of claim 11 wherein applying the electrical signal occurs at a first time, and wherein automatically adjusting the applied signal includes applying the electrical signal at a second time in response to detecting an ejection fraction indicator less than the target ejection fraction threshold.

16. The method of claim 11 wherein automatically adjusting the applied signal includes increasing at least one of an amplitude of the applied signal and a pulse width of the applied signal in response to detecting an ejection fraction indicator less than a target ejection fraction threshold.

17. The method of claim 11 wherein automatically adjusting the applied signal includes decreasing at least one of an amplitude of the applied signal and a pulse width of the applied signal in response to detecting an ejection fraction indicator greater than or equal to a target ejection fraction threshold.

18. The method of claim 11 wherein:
automatically detecting a physiological parameter includes automatically detecting the patient's heart rate; and
automatically adjusting the applied signal includes increasing at least one of an amplitude of the applied signal and a pulse width of the applied signal in response to the increase in the patient's heart rate.

19. The method of claim 11 wherein applying the electrical signal includes applying the signal to the patient via a lead positioned at or proximate to the atrial-ventricular fat pads of the patient's heart.

20. The method of claim 11 wherein applying the electrical signal includes applying the signal with a pulse width less than or equal to 1/(2×the frequency of the signal).

21. The method of claim 11 wherein the treatment system includes an implantable treatment system.

22. The method of claim 11 wherein the at least one detected physiological parameter includes at least one of the patient's heart rate, the patient's blood pressure, and the patient's blood flow rate.

* * * * *

UNITED STATES PATENT AND TRADEMARK OFFICE
CERTIFICATE OF CORRECTION

PATENT NO. : 11,596,798 B2
APPLICATION NO. : 17/030349
DATED : March 7, 2023
INVENTOR(S) : James R. Thacker et al.

It is certified that error appears in the above-identified patent and that said Letters Patent is hereby corrected as shown below:

In the Specification

In Column 1, Line 10, delete "15/414,561" and insert -- 15/414,561, --.

In Column 2, Line 31, delete "("Additional Embodiments")." and insert -- ("Additional Embodiments"). --.

In Column 5, Line 3, delete ""For" and insert -- For --.

In the Claims

In Column 13, Line 39, in Claim 1, delete "heart" and insert -- heart, --.

Signed and Sealed this
Eleventh Day of July, 2023

Katherine Kelly Vidal
*Director of the United States Patent and Trademark Office*